US009561239B2

(12) United States Patent
Jiang et al.

(10) Patent No.: US 9,561,239 B2
(45) Date of Patent: Feb. 7, 2017

(54) COMPOSITIONS AND METHODS FOR INHIBITING NOROVIRUS INFECTION

(71) Applicant: Children's Hospital Medical Center, Cincinnati, OH (US)

(72) Inventors: Xi Jiang, Cincinnati, OH (US); Ming Tan, Cincinnati, OH (US); Xufu Zhang, Guangzhou (CN)

(73) Assignee: Children's Hospital Medical Center, Cincinnati, OH (US)

( * ) Notice: Subject to any disclaimer, the term of this patent is extended or adjusted under 35 U.S.C. 154(b) by 0 days.

(21) Appl. No.: 15/067,337

(22) Filed: Mar. 11, 2016

(65) Prior Publication Data
US 2016/0193229 A1 Jul. 7, 2016

Related U.S. Application Data

(63) Continuation of application No. 14/326,894, filed on Jul. 9, 2014, now Pat. No. 9,321,803.

(60) Provisional application No. 61/845,707, filed on Jul. 12, 2013.

(51) Int. Cl.
| | |
|---|---|
| *A61K 31/56* | (2006.01) |
| *A61K 31/57* | (2006.01) |
| *C07J 41/00* | (2006.01) |
| *C07J 7/00* | (2006.01) |
| *C07J 9/00* | (2006.01) |
| *C07J 3/00* | (2006.01) |
| *A61K 31/568* | (2006.01) |
| *A61K 31/575* | (2006.01) |

(52) U.S. Cl.
CPC .............. *A61K 31/57* (2013.01); *A61K 31/56* (2013.01); *A61K 31/568* (2013.01); *A61K 31/575* (2013.01); *C07J 3/00* (2013.01); *C07J 7/002* (2013.01); *C07J 7/0005* (2013.01); *C07J 9/00* (2013.01); *C07J 9/005* (2013.01); *C07J 41/0005* (2013.01); *C07J 41/0016* (2013.01)

(58) Field of Classification Search
USPC ........................................ 514/177, 178, 181
See application file for complete search history.

(56) References Cited

U.S. PATENT DOCUMENTS

| | | |
|---|---|---|
| 4,547,367 A | 10/1985 | Tabor et al. |
| 4,550,019 A | 10/1985 | Polson |
| 4,916,213 A | 4/1990 | Scannon et al. |
| 5,254,342 A | 10/1993 | Shen et al. |
| 5,326,857 A | 7/1994 | Yamamoto et al. |
| 5,338,689 A | 8/1994 | Yves et al. |
| 5,367,054 A | 11/1994 | Lee |
| 5,559,014 A | 9/1996 | Estes et al. |
| 5,589,453 A | 12/1996 | Greve |
| 5,643,579 A | 7/1997 | Hung et al. |
| 5,665,534 A | 9/1997 | Vandenbergh et al. |
| 5,750,394 A | 5/1998 | Palese et al. |
| 5,783,193 A | 7/1998 | Michael et al. |
| 5,786,340 A | 7/1998 | Henning et al. |
| 5,789,230 A | 8/1998 | Cotton et al. |
| 5,861,241 A | 1/1999 | Herrmann et al. |
| 6,045,854 A | 4/2000 | Prieto et al. |
| 6,130,205 A | 10/2000 | Stapleton et al. |
| 6,140,043 A | 10/2000 | Dierich et al. |
| 6,156,883 A | 12/2000 | Estes et al. |
| 6,187,762 B1 | 2/2001 | Mandeville, III et al. |
| 6,254,867 B1 | 7/2001 | Reiser et al. |
| 6,258,789 B1 | 7/2001 | German et al. |
| 6,300,090 B1 | 10/2001 | Steinman et al. |
| 6,475,489 B1 | 11/2002 | Rutter et al. |
| 6,572,862 B1 | 6/2003 | Estes et al. |
| 6,593,080 B1 | 7/2003 | Smith |
| 6,942,865 B2 | 9/2005 | Estes et al. |
| 6,946,266 B2 | 9/2005 | Neiman |
| 7,785,871 B2 | 8/2010 | Reed |
| 7,893,041 B2 | 2/2011 | Morrow et al. |
| 7,912,484 B2 | 3/2011 | Sohn et al. |
| 7,977,098 B2 | 7/2011 | Jiang et al. |
| 8,026,221 B2 | 9/2011 | Jiang et al. |
| 8,277,819 B2 | 10/2012 | Jiang et al. |
| 8,475,789 B2 | 7/2013 | Bisgaard-Frantzen et al. |
| 8,486,421 B2 | 7/2013 | Jiang et al. |
| 9,096,644 B2 | 8/2015 | Tan et al. |

(Continued)

FOREIGN PATENT DOCUMENTS

| | | |
|---|---|---|
| AU | 2003273206 | 12/2009 |
| AU | 2009238339 | 6/2011 |

(Continued)

OTHER PUBLICATIONS

Remington 21st Edition pp. 89, 720-722. Published 2005.*

(Continued)

*Primary Examiner* — Timothy Thomas
*Assistant Examiner* — George W Kosturko
(74) *Attorney, Agent, or Firm* — Frost Brown Todd LLC

(57) ABSTRACT

A composition for use in inhibiting the binding of a Norovirus to the histo-blood group antigen on the surface of epithelia is disclosed. The composition may contain a therapeutically effective amount of a binding-inhibiting compound and a carrier and/or excipient. The compounds may competitively bind a Norovirus that has the capability of binding with the histo-blood group antigens of secretor blood type, including A, B, AB, and O blood types. The compositions may be administered to a human prior to or after infection by a Norovirus, to prevent, ameliorate, or reduce the effects of an infection.

2 Claims, 12 Drawing Sheets

(56) References Cited

U.S. PATENT DOCUMENTS

| | | |
|---|---|---|
| 2002/0019991 A1 | 2/2002 | Prieto et al. |
| 2006/0057562 A1 | 3/2006 | Jiang et al. |
| 2007/0231320 A1 | 10/2007 | Cook et al. |
| 2007/0280949 A1 | 12/2007 | Alfa |
| 2008/0085553 A1 | 4/2008 | Reed et al. |
| 2011/0152263 A1 | 6/2011 | Jiang et al. |
| 2012/0009211 A1 | 1/2012 | Tschopp et al. |
| 2012/0141458 A1 | 6/2012 | Starzl |
| 2014/0017257 A1 | 1/2014 | Jiang et al. |
| 2015/0293768 A1 | 10/2015 | Miyoshi et al. |

FOREIGN PATENT DOCUMENTS

| | | | | |
|---|---|---|---|---|
| CA | 2487846 | | 12/2003 | |
| CN | 1330080 | | 1/2002 | |
| EP | 1532279 | | 5/2005 | |
| JP | 2012-529298 | A | 11/2012 | |
| JP | 2015-201119 | | 11/2015 | |
| WO | WO 0108677 | A1 * | 2/2001 | ............ A61K 31/00 |
| WO | WO 0230409 | A2 * | 4/2002 | ............ A61K 31/57 |
| WO | WO 03/003985 | | 1/2003 | |
| WO | WO 03/101176 | | 12/2003 | |
| WO | WO 2005/030806 | A2 | 4/2005 | |
| WO | WO 2005/032457 | A2 | 4/2005 | |
| WO | WO 2006/138514 | A2 | 12/2006 | |
| WO | WO 2007/020017 | A1 | 2/2007 | |
| WO | WO 2007103162 | A2 * | 9/2007 | ............ A61K 31/57 |
| WO | WO 2010/144602 | | 12/2010 | |
| WO | WO 2011/120044 | A1 | 9/2011 | |

OTHER PUBLICATIONS

Di et al (Solvent Systems and Their Selection in Pharmaceutics and Biopharmaceutics: Biotechnology Pharmaceutical Aspects vol. VI pp. 111-136. Published 2007).*

Molport HTS Library Product Page for compounds 002-511-430 and 002-516-186 (Published online 2011). CAS Registry of compounds 002-511-430 and 002-516-186 indexed on Oct. 14, 1997 and Jul. 11, 2008.*

Adler, et al., "High Affinity Binding of the *Entamoeba histolytica* Lectin to Polyvalent *N*-Acetylgalactosaminides", Mar. 10, 1995, The Journal of Biol. Chem., vol. 270, No. 10, pp. 5164-5171.

Affixed, WordReference.com, English Dictionary, search for word "affixed", searched on Jan. 16, 2010, in corresponding U.S. Appl. No. 11/264,992.

Akita, E.M., et al., "Immunoglobulins from Egg-Yolk: Isolation and Purification", 1992, Journal of Food Science, 57, 629-634.

Akita, E.M., et al., "Production and purification of Fab' fragments from chicken egg yolk immunoglobulin Y (IgY)", 1993, K. Immunol Methods, 162, 155-64.

Amaral, J.A., et al., "Antienteropathogenic *Escherichia coli* immunoglobulin Y isolated from eggs laid by immunized Leghorn chickens", 2002, Res Vet Sci, 72, 229-34.

Assay, http://encycolpedia.thefreedictionary.com/assay, in corresponding U.S. Appl. No. 11/264,992, printed on Feb. 22, 2008, p. 1-5.

Atmar, R., et al., "Diagnosis of Non-cultivatable Gastroenteritis Viruses, the Human Caliciveruses", Jan. 2001, Clinical Microbiology Reviews, vol. 14, No. 1, pp. 15-37.

Bereszczak et al., "Structure, stability and dynamics of norovirus P domain derived protein complexes studied by native mass spectrometry," Journal of Structural Biology, Feb. 2012, 177(2):273-282.

Bertolotti-Ciarlet et al., "Structural Requirements for the Assembly of Norwalk Virus-Like Particles," J Virol, Apr. 2002, 76(8):4044-4055.

Biesiada, J., et al., "On setting up and assessing docking simulations for virtual screening," Methods in molecular biology (Clifton, NJ), 2012, 928:1-16.

Biesiada, J., et al., "Survey of public domain software for docking simulations and virtual screening," Human genomics, 2011, 5:497-505.

Brinker, J.P., et al., "Immunoglobulin M Antibody Test to Detect Genogroup II Norwalk-Like Virus Infection", Sep. 1999, Journal for Clinical Microbiology, vol. 37, No. 9, 2983-2986.

Bruss, V., et al., "Mutational Analysis of Hepatitis B Surface Antigen Particle Assembly and Secretion," J Virol, Jul. 1991, 65(7):3813-3820.

Bu, W., et al., "Structural basis for the receptor binding specificity of Norwalk virus," J Virol, 2008, 82:5340-5347.

Burton-MacLeod, J.A., et al., "Evaluation and Comparison of Two Commercial Enzyme-Linked Immounosorbent Assay Kits for Detection of Antigenically Diverse Human Noroviruses in Stool Samples," Journal of Clinical Microbiology, Jun. 2004, 42(6):2587-2595.

Cao, S., et al., "Structural basis for the recognition of blood group trisaccharides by norovirus," J Virol, 2007, 81:5949-5957.

Capua, et al., "Control and prevention of avian influenza in an evolving scenario," Vaccine, 2007, 25:5645-5652.

Cavasotto, C.N., et al., "Ligand docking and structure-based virtual screening in drug discovery," Current topics in medicinal chemistry, 2007, 7:1006-1014.

Centers for Disease Control and Prevention Information Page, CDC-Norovirus: Q&A, accessed online at http://www.cdc.gov/ncidod/dvrd/revb/gastro/norovirus-qa.htm Sep. 29, 2010.

Centers for Disease Control and Prevention, Norovirus Illness: Key Facts, 2015, Accessed online Feb. 9, 2015 at http://www.cdc.gov/norovirus/about/treatment.html.

Centers for Disease Control and Prevention, Rotavirus vaccination, accessed online on Feb. 9, 2015 at http://www.cdc.gov/vaccines/vpd-vac/rotavirus/default.htm.

Chakravarty et al., "Evolutionary Trace Residues in Noroviruses: Importance in Receptor Binding, Antiagenicity, Virion Assembly, and Strain Diversity," J Virol, Jan. 2005, 79(1):554-568.

Chang, D.T., et al., "MEDock: a web server for efficient prediction of ligand binding sites based on a novel optimization algorithm," Nucleic Acids Res, 2005, 33:W233-238.

Chatterji, et al., "Chemical conjugation of heterologous proteins on the surface of Cowpea mosaic virus", Bioconjug Chem, 2004, 15:807-13.

Chatterji, A., et al., "Cowpea Mosaic Virus: From the Presentation of Antigenic Peptides to the Display of Active Biomaterials," Intervirology, 2002, 45(4-6):362-370.

Chen, C., et al., "Nanoparticle-templated assembly of viral protein Cages," Nano Lett, 2006, 6:611-615.

Chen, J.H., et al., "ChemDB update—full-text search and virtual chemical space," Bioinformatics, 2007, 23:2348-2351.

Chen, Y., et al., "Crystallography of a lewis-binding norovirus, elucidation of strain-specificity to the polymorphic human histo-blood group antigens," PLoS pathogens, 2011, 7:e1002152.

Chen, et al., "Inter-and Intragenus Structural Variation in Caliciviruses and Their Functional Implications", J. Virol, Jun. 2004, vol. 78, No. 12, pp. 6469-79.

Chen, et al., "Packaging of gold particles in viral capsids", J Nacosci Nanotechnol, 2005, 5:2029-33.

Choi, A.H., et al. "Functional Mapping of Protective Domains and Epitopes in the Rotavirus VP6 Protein," J Virol, Dec. 2000, 74(24):11574-11580.

Choi, A.H., et al., "Functional mapping of protective epitopes within the rotavirus VP6 protein in mice belonging to different haplotypes," Vaccine, Jan. 2003, 21(7-8):761-767.

Choi, J.M., et al., "Atomic resolution structural characterization of recognition of histo-blood group antigens by Norwalk virus," Proc Natl Acad Sci USA, 2008, 105:9175-9180.

Chupakhin, et al., "An unusually easy oxidative dequarternization of N-alkyl-1,2,4-triazinium salts," Mendeleev Communications, 1995, 3:104-105, CAPLUS Abstract, Doc No. 123:285918.

Cooper, H.M., et al., "Production of polyclonal antisera", 2009, Curr Protoc Neurosci, 2009, Chapter 5, Unit 5.5.

Crisci et al., "Chimeric calicivirus-like particles elicit protective anti-viral Cytotoxic responses without adjuvant," Virol, May 2009, 387(2):303-312.

(56) References Cited

OTHER PUBLICATIONS

De Rougemont, A., et al., "Qualitative and quantitative analysis of the binding of GII.4 norovirus variants onto human blood group antigens," J Virol, 2011, 85:4057-4070.

Dias da Silva, et al., "IgY: a promising antibody for use in immunodiagnostic and in immunotherapy", 2010, Vet Immunol Immunopathol, 135, 173-80.

Douglas, et al., "Viruses: making friends with old foes", Science, 2006, 312:873-75.

Douglas, T., "A bright bio-inspired future", Science, 2003, 299:1192-93.

Dragnea, et al., "Gold nanoparticles as spectroscopic enhancers for in vitro studies on single viruses", J Am Chem Soc, 2003, 125:6375-75.

Eldon Biologicals A/S, Eldoncar Home Kit 2511 Manufacture Catalog, published on website, searched on Sep. 2008, in corresponding U.S. Appl. No. 11/264,992.

Eldon Biologicals A/S, Eldoncar Home Kit 2511 Manufacture Protocol, published on website, searched on Sep. 2008, in corresponding U.S. Appl. No. 11/264,992.

EldonCard Home Blood Testing kit Published on Website, searched on Sep. 2008, in corresponding U.S. Appl. No. 11/264,992.

Erdman, D.D., et al., "Serum Immunoglobulin A Response to Norwalk Virus Infection", Jun. 1989, Journal of Clinical Microbiology, vol. 27, No. 6, pp. 1417-1418.

Estes, M., et al., "Norwalk Virus Vaccines: Challenges and Progress", 2000, The Journal of Infectious Diseases, vol. 181, Suppl. 2, pp. S367-S373.

Evaluation Report for Eldon Biologicals A/S, published 2004, in corresponding U.S. Appl. No. 11/264,992.

Farkas, T., et al., "Homologous versus Heterologous Immune Responses to Norwalk-Like Viruses among Crew Members after Acute Gastroenteritis Outbreaks on 2 Navy Vessels", Jan. 2003, The Journal of Infectious Diseases, vol. 187, pp. 187-193.

Farkas, T., et al., "Molecular Detection and Sequence Analysis of Human Caliciviruses From Acute Gastroenteritis Outbreaks in Hungary", Jan. 2002, Journal of Medical Virology, vol. 67, pp. 567-573.

Feng, X., et al., "Library screen for inhibitors targeting norovirus binding to histo-blood group antigen receptors," Antimicrob Agents Chemother, 2007, 51:324-331.

Feng, Z.K., et al., "Ligand Depot: a data warehouse for ligands bound to macromolecules," Bioinformatics, 2004, 20:2153-2155.

GenBank: AFA25718.1, VP4, partial [Human rotavirus], 2012.

Glass, R.I., et al., "Norovirus gastroenteritis," N Engl J Med, 2009, 361:1776-1785.

Gray, J.J., et al., "Prevalence of Antibodies to Norwalk Virus in England: Detection by Enzyme-Linked Immunosorbent Assay Using Baculovirus-Expressed Norwalk Virus Capsid Antigen", Apr. 1993, Journal of Clinical Microbiology, vol. 31, No. 4, pp. 1022-1025.

Green, J., et al., "Capsid protein diversity among the Norwalk-like viruses", 2000, Virus Genes, 20:227-36. (Abstract).

Green, K.Y., et al., "Taxonomy of the Caliciviruses", 2000, The Journal of Infectious Diseases, vol. 181 (Suppl 2), pp. S322-330.

Grgacic, et al., "Virus-like particles: passport to immune recognition," Methods, Spet. 2006, 40(1):60-65.

Guix, S., et al., "Norwalk Virus RNA Is Infectious in Mammalian Cells," J. Virol., 2007, 81(22):12238-12248.

Hale, A.D., et al., "Expression and Self-Assembly of Grimsby Virus: Antigenic Distinction from Norwalk and Mexico Viruses", Jan. 1999, Clinical and Diagnostic Laboratory immunology, vol. 6, No. 1, pp. 142-145.

Hale, A.D., et al., "Identification of an Epitope Common to Genogroup 1 'Norwalk-Like Viruses'", Apr. 2000, Journal of Clinical Microbiology, vol. 38, No. 4, pp. 1656-1660.

Hansman, G.S., et al., "Crystal Structures of GII.10 and GII.12 Norovirus Protruding Domains in Complex with Histo-Blood Group Antigens Reveal Details for a Potential Site of Vulnerability," J Virol, 2011, 85:6687-6701.

Hardy et al., "Specific Proteolytic Cleavage of Recombinant Norwalk Virus Capsid Protein," J Virol, Mar. 1995, 69(3):1693-1698.

Harrington, P., et al., "Binding Norwalk Virus-Like Particles to ABH Histo-Blood Group Antigens is Blocked by Antisera from Infected Human Volunteers or Experimentally Vaccinated Mice", Dec. 2002, Journal of Virology, vol. 76, No. 23., pp. 12335-12343.

Harrington, P., et al., "Norovirus Capture with Histo-Blood Group Antigens Reveals Novel Virus-Ligand Interactions", Mar. 2004, Journal of Virology, vol. 78, No. 6, pp. 2035-3045.

Hennessy, E.P., et al., "Norwalk Virus Infection and Disease is Associated with ABO Histo-Blood Group Type", 2003, The Journal of Infectious Diseases, vol. 188, pp. 176-177.

Hetenyi, C., et al., "Efficient docking of peptides to proteins without prior knowledge of binding site," Protein science: a publication of the Protein Society, 2002, 11:1729-1737.

Hoffman, R., ed., *Hematology Basic Principles and Practice*, 2nd Ed., 1995, Churchill Livingston NY, NY.

Huang et al., "Noroviruses Bind to Human ABO, Lewis, and Secretor Histo-Blood Antigens: Identification of 4 Distinct Strain-Specific Patterns," J Infect Dis, Jul. 2003, 188:19-31.

Huang, P., et al., "Norovirus and histo-blood group antigens: demonstration of a wide spectrum of strain specificities and classification of two major binding groups among multiple binding patterns," J Virol, 2005, 79(11):6714-6722.

Hutson, A., et al., "Norwalk Virus-Like Particle Hemagglutination by Binding to H Histo-Blood Group Antigens", Jan. 2003, Journal of Virology, vol. 77, No. 1, pp. 405-415.

Hutson, A.M., et al. "ABO Phenotype Associated with Norwalk Virus Infection and Disease may be Related to Norwalk Virus-Like particle Binding H Antigens", Apr. 2002), Gastroenterology, vol. 122, No. 4, Suppl. 1, pp. A-141. XP009054158 & Digestive Disease Week and the 103rd annual Meeting of the American Gastroenterological Association; San Francisco, CA, USA; May 19-22, 2002.

Hutson, A.M., et al., "Norwalk Virus Infection and Disease is Associated with ABO Histo-Blood Group Type", 2002, The Journal of Infectious Diseases, 185, pp. 1335-1337.

Immuncor Inc., Manufacture Advertisement, published on Immucor Website, searched Sep. 2008, in corresponding U.S. Appl. No. 11/264,992.

Irwin, J.J. et al., "ZINC—A Free Database of Commercially Available Compounds for Virtual Screening," J. Chem. Inf. Model., 2005, 45(1), pp. 177-182.

Irwin, J.J. et al., "ZINC: A Free Tool to Discover Chemistry for Biology," J. Chem. Inf. Model., 2012, 52(7), pp. 1757-1768.

Jennings et al., "The coming of age of virus-like particle vaccines," Biol Chem, May 2008, 389(5):521-536.

Jiang et al., Expression, Self-Assembly, and Antigenicity of the Norwalk Virus Capsid Protein, J Virol, Nov. 1992, 66(11):6527-6532.

Jiang, X., et al., "Expression, Self-Assembly, and Antigenicity of a Snow Mountain Agent-Like Calicivirus Capsid Protein", Jun. 1995, Journal of Clinical Microbiology, vol. 33, No. 6, pp. 1452-1455.

Jiang, X., et al., "Baculavirus expression and antigenic characterization of the capsid proteins of three Norwalk-like viruses," Archives of Virology, 2002, 147:119-130.

Jiang, X., et al., "Human Milk Contains Elements That Block Binding of Noroviruses to Human Histo-Blood Group Antigens in Saliva," J Infect Diseases, Nov. 2004, 190:1850-1859.

Jiang, X., et al., "Norwalk Virus Genome Cloning and Characterization," Science, Dec. 1990, 250:1580-1583.

Jiang, X., et al., "Sequence and Genomic Organization of Norwalk Virus," Virol, 1993, 195:51-61.

Kit, http://acronyms.thefreedictionary.com/kit, in corresponding U.S. Appl. No. 11/264,992, printed on Feb. 22, 2008, p. 1-4.

Kubota, T., et al., "Structural basis for the recognition of Lewis antigens by genogroup I norovirus," J Virol, 2012, 86:11138-11150.

Kumar, S., et al., "MEGA2: molecular evolutionary genetics analysis software", 2001, Bioinformatics Applications Note, vol. 17, No. 12, pp. 1244-1245.

Kurdyashov, et al., "Characterization of a mouse monoclonal IgG3 antibody to the tumor-associated globo H structure produced by

(56) References Cited

OTHER PUBLICATIONS

Immunization with a synthetic glycoconjugate", 1998, Glycoconjugate Journal, vol. 15, pp. 243-249.
Lancel, M., et al., "Allopregnanolone Affects Sleep in a Benzodiazepine-Like Fashion," The Journal of Pharmacology and Experimental Therapeutics, 1997, 282-1213-1218, 6 pgs.
Lavanchy, et al., "Worldwide epidemiology of HBV infection, disease burden, and vaccine prevention," J Clin Virol, 2005, 34(suppl 1):S1-S3.
Lew, J.F., et al., "Molecular Characterization of Hawaii Virus and Other Norwalk-like Viruses: Evidence for Genetic Polymorphism among Human Caliciviruses", Mar. 1994, The Journal of Infectious Diseases, vol. 170, pp. 535-542.
Lindesmith, L., et al., "Human Susceptibility and Resistance to Norwalk Virus Infection", May 2003, Natural Medicine, vol. 9, No. 5, p. 548-553.
Liou, J.F., et al. "Passive protection effect of chicken egg yolk immunoglobulins on enterovirus 71 infected mice", 2010, Vaccine, 28, 8189-96.
Lopman, B., et al., "Environmental transmission of norovirus gastroenteritis," Curr Opin Virol, 2012, 2:96-102.
Manayani, D.J., "A Viral Nanoparticle with Dual Function as an Anthrax Antitoxin and Vaccine," PLoS Pathog., Oct. 2007, 3(10):1422-1431.
Marionneau, S., et al., "ABH and Lewis Histo-Blood Group Antigens, A Model for the Meaning of Oligosaccharide Diversity in the Face of a Changing World", Jul. 2001, Biochimie, 83(7):565-73.
Marionneau, S., et al., "Norwalk Virus Binds to Histo-Blood Group Antigens Present on Gastroduodenal Epithelial Cells of Secretor Individuals", Jun. 2002, Gastroenterology, 122, pp. 1697-1777.
McNeal, M.M., et al., "Antibody-Dependant and -Independent Protection following Intranasal Immunization of Mice with Rotavirus Particles," J Virol, Sep. 1999, 73(9):7565-7573.
Merriam-Webster's Collegiate Dictionary, Tenth Edition copyright 1998 by Merriam-Webster, Inc., p. 924.
Morris, G.M., et al., "Automated docking using a Lamarckian genetic algorithm and an empirical binding free energy function," Journal of Computational Chemistry, 1998, 16:1639-1662.
National Cancer Institute, Downloadable Structure Files of NCI Open Database Compounds, Release 4 File Series, May 2012, 4 pgs.
Nguyen, H.H., et al., "Prophylactic and therapeutic efficacy of avian antibodies against influenza virus H5N1 and H1N1 in mice", 2010, PLoS One, 5, e10152.
Nicolas, K.B., et al., "GeneDoc: Analysis and Visualization of Genetic Variation", http://www.psc.edu/biomed/genedoc/ebinet.htm, pp. 1-5.
Norovirus Fact Sheet, Minnesota Department of Health, updated Nov. 16, 2010, 2 pgs.
Nurminen, K., et al., "Prevalence of norovirus GII-4 antibodies in Finnish children", 2011, J Med Virol, 83, 525-31.
Ochoa, et al., "Generation and structural analysis of reactive empty particles derived from an icosahedral virus", Chem Biol, 2006, 13:771-78.
Oriol, R., et al., "Insights into the Expression of ABH and Lewis Antigens through Human Bone Marrow Transplantation", 1981, Am Journal Hum Genet, vol. 33, pp. 551-560.
Patel, et al., "Noroviruses: A comprehensive review," J Chem Virol, 2009, 44:1-8.
Patel, M.M., et al., "Systematic literature review of role of noroviruses in sporadic gastroenteritis," Emerg Infect Dis, 2008, 14:1224-1231.
Peabody, D.S., "A Viral Platform for Chemical Modification and Multivalent Display", J Nanobiotechnology, 2003, 1:5.
Pelosi, E., et al., "The Seroepidemiology of Genogroup 1 and Genogroup 2 Norwalk-Like Viruses in Italy", Apr. 1, 1999, Journal of Medical Virology, vol. 58, issue 1, pp. 93-99.
Prasad et al., "X-ray Crystallographic Structure of the Norwalk Virus Capsid," Science, Oct. 1999, 286:287-290.
Radloff, et al., "Metal nanoshell assembly on a virus bioscaffold", Nano Lett, 2005, 5:1187-91.
Reeck, A., et al., "Serological correlate of protection against norovirus-induced gastroenteritis", 2010, J Infect Dis, 202, 1212-8.
Schwartz, S., et al., "Norovirus gastroenteritis causes severe and lethal complications after chemotherapy and hematopoietic stem cell transplantation", 2011, Blood, 117, 5850-6.
Shanker, S., et al., "Structural analysis of histo-blood group antigen binding specificity in a norovirus GII.4 epidemic variant: implication for epochal evolution," J Virol, 2011, 85:8635-8645.
Silverman, *The Organic Chemistry of Drug Design and Drug Action*, 1992, Academic Press, pp. 4-47.
Sixth International Symposium on Positive Strand RNA Viruses (May 28-Jun. 2, 2001). Institut Pasteur, Paris, France; Scientific Program Abstracts "Norwalk Virus Binds to H Type 1 Histo-Blood Group Antigen Present on Gastro-Duodenal Epithelial Cells of 'Secretor' Phenotype Individuals".
Tamura, M., et al., "Interaction of Recombinant Norwalk Virus Particles with the 105-Kilodalton Cellular Binding Protein, a Candidate Receptor molecule for Virus Attachment", Dec. 2000, Journal of Virology, vol. 74, No. 24, pp. 11589-11597.
Tan et al., "Norovirus P. Particle, a Novel Platform for Vaccine Development and Antibody Protection," J Virol, Jan. 2011, 85(2):753-764.
Tan et al., "The formation of P particle increased immunogenicity of norovirus P protein," Immunology, May 2012, 136:28-29.
Tan, et al., "*E. coli*-Expressed Recombinant Norovirus Capsid Proteins Maintain Authentic Antigenicity and Receptor Binding Capability," J Med Virol, 2004, 74(4):641-649.
Tan, M., et al., "Conservation of carbohydrate binding interfaces: evidence of human HBGA selection in norovirus evolution," PLoS One, 2009, 4:e5058.
Tan, M., et al., "C-terminal arginine cluster is essential for receptor binding of norovirus capsid protein," J Virol, 2006, 80:7322-7331.
Tan, M., et al., "Elucidation of strain-specific interaction of a GII-4 norovirus with HBGA receptors by site-directed mutagenesis study," Virology, 2008, 379:324-334.
Tan, M., et al., "Mutations within the P2 domain of norovirus capsid affect binding to human histo-blood group antigens: evidence for a binding pocket," J Virol, 2003, 77(23):12562-12571.
Tan, M., et al., "Noroviral P particle: Structure, function and applications in virus-host interaction," Virology, 2008, 382:115-123.
Tan, M., et al., "Norovirus P particle: a subviral nanoparticle for vaccine development against norovirus, rotavirus and influenza virus" Nanomedicine, Jun. 2012, 7(6):889-897.
Tan, M., et al., "Norovirus and its histo-blood group antigen receptors: an answer to a historical puzzle," Trends Microbiol, 2005, 13(6):285-293.
Tan, M., et al., "Norovirus gastroenteritis, carbohydrate receptors, and animal models," PLoS pathogens, 2010, 6:e1000983.
Tan, M., et al., "Norovirus-host interaction: implications for disease control and prevention," Expert Rev Mol Med, 2007, 9:1-22.
Tan, M., et al., "Terminal modifications of norovirus P domain resulted in a new type of subviral particles, the small P particles," Virology, 2011, 410:345-352.
Tan, M., et al., "The P domain of norovirus capsid protein forms dimer and binds to histo-blood group antigen receptors," J Virol, 2004, 78(12):6233-6242.
Tan, M., et al., "The p domain of norovirus capsid protein forms a subviral particle that binds to histo-blood group antigen receptors," J Virol, 2005, 79(22):14017-14030.
Tan, M., "Norovirus-host interaction: Multi-selections by human histo-blood group antigens," Trends in microbiology, 2011, 19:382-388.
Taube, S., Murine noroviruses bind glycolipid and glycoprotein attachment receptors in a strain-dependent manner, J Virol, 2012, 86:5584-5593.
Tini, M., et al., "Generation and application of chicken egg-yolk antibodies," Comparative Biochemistry and Physiology Part A, 2002, 131:569-574.
Treanor, J.J. et al., "Development of an Enzyme Immunoassay for the Hawaii Agent of Viral Gastroenteritis", Dec. 1988, Journal of Virol Methods, 22(2-3):207-14.

(56) References Cited

OTHER PUBLICATIONS

UniProtKB—H6WUJ8 (H6WUJ8_9REOV), Outer capsid protein VP4, 2012.
UniProtKB/Swiss Prot: Q913Z3 (2006), via PubMed.
Vega, C., et al., "Egg yolk IgY: protection against rotavirus induced diarrhea and modulatory effect on the systemic and mucosal antibody responses in newborn calves", 2011, Vet Immunol Immunopathol, 142, 156-69.
Villoutreix, B.O., et al., "Structure-based virtual ligand screening: recent success stories," Combinatorial chemistry & high throughput screening, 2009, 12:1000-1016.
Wang, L., et al., "Polyvalent complexes for vaccine development", Biomaterials, 2013, 34, pp. 4480-4492.
White et al., "Attachment and Entry of Recombinant Norwalk Virus Capsids to Cultured human and Animal Cell Lines," J Virol, Oct. 1996, 70(10):6589-6597.
White et al., "Biochemical Characterization of a Smaller Form of Recombinant Norwalk Virus Capsids Assembled in Insect Cells," J Virol, Oct. 1997, 71(10):8066-8072.
Wobus, C.E., et al., "Replication of Norovirus in Cell Culture Reveals a Tropism for Dendritic Cells and Macrophages", Dec. 2004, PLoS Biology, vol. 2, Issue 12, pp. 0001-9.
Wolf, A., et al., "In silico drug discovery approaches on grid computing infrastructures," Current clinical pharmacology, 2010, 5:37-46.
Xia, M., et al., "A candidate dual vaccine against influenza and noroviruses", Vaccine, Oct. 13, 2011, 29(44): 7670-7677.
Xia, M., et al., "Norovirus Capsid Protein Expressed in Yeast Forms Virus-like Particles and Stimulates Systemic and Mucosal Immunity in Mice Following an Oral Administration of Raw yeast Extracts," J Med Virol, Jan. 2007, 79(1):74-83.
Xu, Y., et al., "Application of chicken egg yolk immunoglobulins in the control of terrestrial and aquatic animal diseases: A review", 2011, Biotechnol Adv., 29:860-868.
Yang, Y., et al., *capsid protein, partial*, GenBank: ADF50093.1, submitted Feb. 24, 2010.
Zhang, X.F., et al., "Tannic acid inhibited norovirus binding to HBGA receptors, a study of 50 Chinese medicinal herbs," Bioorg Med Chem, 2012, 20:1616-1623.
Zheng, D.P., et al., "Molecular epidemiology of genogroup II-genotype 4 noroviruses in the United States between 1994 and 2006," J Clin Microbiol, 2010, 48:168-177.
Australian Information Statement Documentary Search Results dated May 16, 2007 for Application No. AU 2003273206.
Canadian Office Action dated Jan. 26, 2010 for Application No. CA 2,487,846.
Canadian Response and Amendment filed Jul. 16, 2010 for Application No. CA 2,487,846.
Canadian Response and Amendment filed Mar. 3, 2011 for Application No. CA 2,487,846.
Chinese Office Action dated Jul. 11, 2013 for Application No. CN 201080035302.2.
Chinese Office Action, Second, dated Apr. 28, 2014, for Application No. CN 201080035302.2.
International Search Report dated Jan. 14, 2005 for Application No. PCT/US03/17247.
International Preliminary Examination Report dated Mar. 21, 2005 for Application No. PCT/US03/17247.
International Search Report dated Apr. 23, 2007 for Application No. PCT/US2006/023407.
International Preliminary Report on Patentability and Written Opinion dated Dec. 17, 2007 for Application No. PCT/US2006/023407.
International Search Report and Written Opinion dated Mar. 31, 2011 for Application No. PCT/US2010/038008, 10 pgs.
International Preliminary Report on Patentability dated Dec. 22, 2011 for Application No. PCT/US2010/038008, 6 pgs.
International Search Report and Written Opinion dated Oct. 16, 2013 for Application No. PCT/US2013/050004.
Supplementary European Search Report dated Jan. 7, 2013 for Application No. EP 10786797.0, 5 pgs.
Supplementary Partial European Search Report dated Sep. 20, 2005 for Application No. EP 03 74 1844.
U.S. Appl. No. 60/385,283, filed May 31, 2002.
U.S. Appl. No. 60/385,296, filed May 31, 2002.
U.S. Appl. No. 60/691,172, filed Jun. 16, 2005.
U.S. Appl. No. 61/185,564, filed Jun. 9, 2009.
U.S. Appl. No. 61/224,696, filed Jul. 10, 2009.
U.S. Appl. No. 61/670,288, filed Jul. 11, 2012.
U.S. Appl. No. 61/670,361, filed Jul. 11, 2012.
U.S. Appl. No. 61/845,707, filed Jul. 12, 2013.

\* cited by examiner

COMPOSITIONS AND METHODS FOR INHIBITING NOROVIRUS INFECTION

CROSS-REFERENCE TO RELATED APPLICATIONS

This application is a continuation of and claims priority to U.S. patent application Ser. No. 14/326,894, filed Jul. 9, 2014 entitled "Compositions and Methods for Inhibiting Norovirus Infection," which claims the benefit of U.S. Application Ser. No. 61/845,707, filed Jul. 12, 2013, both of which are incorporated herein by reference in their entirety for all purposes.

GOVERNMENT RIGHTS

This invention was made with government support under W81XWH-04-1-0066 awarded by the U.S. Army Medical Research and Material Command and AI055649 and AI037093 awarded by the National Institutes of Health. The government has certain rights in the invention.

BACKGROUND

Noroviruses (NoVs) are a group of single-stranded, positive sense RNA viruses constituting the Norovirus genus in the family Caliciviridae. NoVs have been recognized as the most important cause of viral epidemic acute gastroenteritis affecting people of all ages [1,2]. In the United States NoVs cause 23 million infections each year and are responsible for more than 90% of the outbreaks of viral gastroenteritis. On a worldwide basis NoVs lead to 218,000 deaths in developing countries and 1.1 million episode of pediatric gastroenteritis in developed countries annually [3]. Thus, NoV associated diseases have been a heavy burden to public healthcare. NoVs are difficult to control owing to their widespread nature and the lack of effective vaccines and antivirals.

NoVs are small (about 38 nm in diameter), non-enveloped, single-stranded, and positive-sense RNA viruses belonging to the family Caliciviridae. The NoV genome encodes three open reading frames (ORF) in which ORF-2 encodes one major structure protein of about 60 kDa that spontaneously forms virus-like particles (VLPs) when expressed in baculovirus or in other expression systems. These VLPs are morphologically and antigenically indistinguishable from the native forms of viruses found in human stools, providing valuable materials for development of immunological assays, for study of virus-host interaction, as a candidate vaccine, and for determination of the structure and capsid assembling of NoVs.

NoVs are known to recognize human histo-blood group antigens (HBGAs) as receptors. HBGAs are complex carbohydrates linked to glycoproteins or glycolipids that are present on the surfaces of red blood cells and mucosal epithelial cells or as free oligosaccharides in biological fluids such as blood, saliva, milk, and intestinal contents. The HBGA system is controlled by multiple gene families that contain silent alleles, and three major HBGA families, the Lewis, secretor, and ABO families, are involved in NoV infection. The recognition of HBGAs by NoVs has been found to be highly specific; different NoVs recognize different HBGAs, and so far eight distinct receptor-binding patterns have been identified. According to potentially shared antigenic epitopes among different NoVs (the A, B, H and Lewis epitopes), the eight binding patterns can be sorted into two groups: the A/B and the Lewis (non-secretor) binding groups. Strains in the A/B binding groups bind to the A and/or B or H epitopes but not the Lewis epitopes, while strains in the Lewis binding group recognize the Lewis and H epitopes but not the A and B epitopes.

The association of HBGAs with NoV infection has been demonstrated by human volunteer studies wherein the attachment of NoV to the intestinal epithelium via a matched HBGA receptor is a prerequisite for NoV infection. Inhibition of this interaction may result in prevention or control of the viral infection.

Currently there is no effective intervention available against NoV gastroenteritis. The present disclosure addresses the long felt need for compounds useful in the prevention and/or treatment of NoV infection.

BRIEF SUMMARY

Disclosed are compositions and methods useful for inhibiting and/or controlling the binding of a Norovirus to a histo-blood group antigen. Further disclosed are compositions and methods for the treatment and/or prevention of NoV infection.

DETAILED DESCRIPTION

Figure 1A:
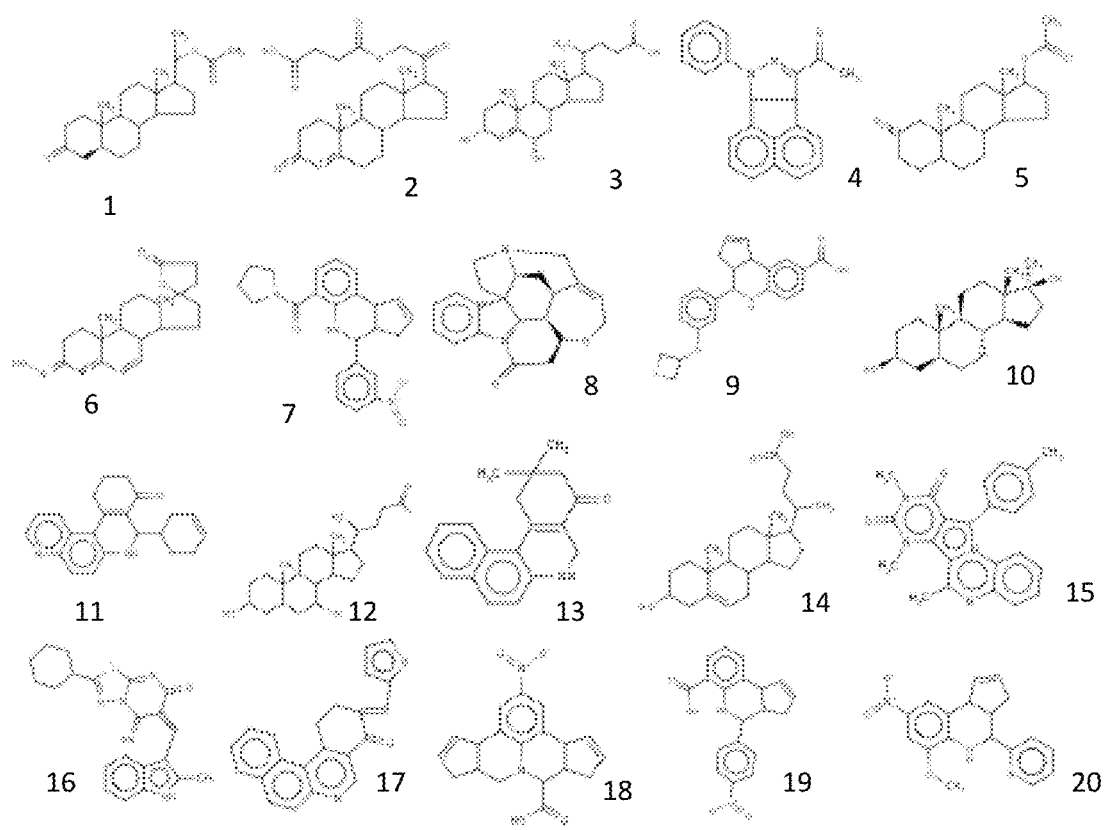
FIGS. 1A-1H depict the 160 top hits including ZINC numbers and structures.
Figure 1B:
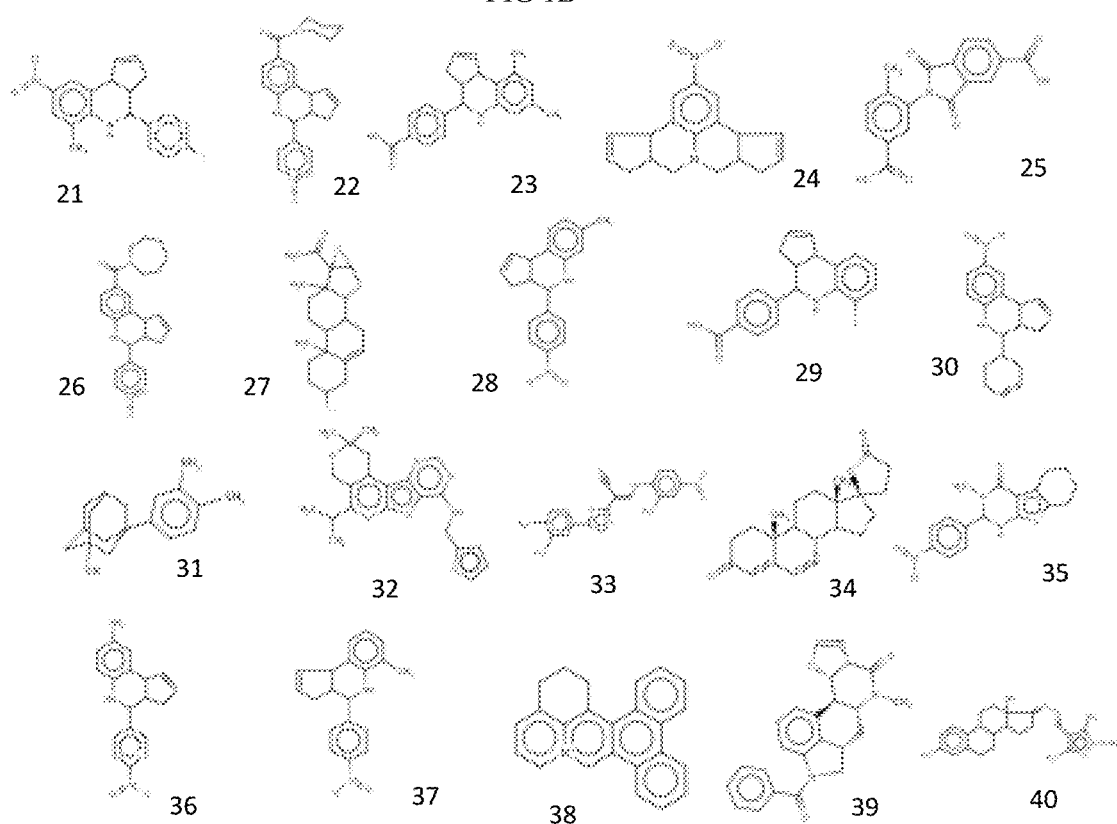
Figure 1C:
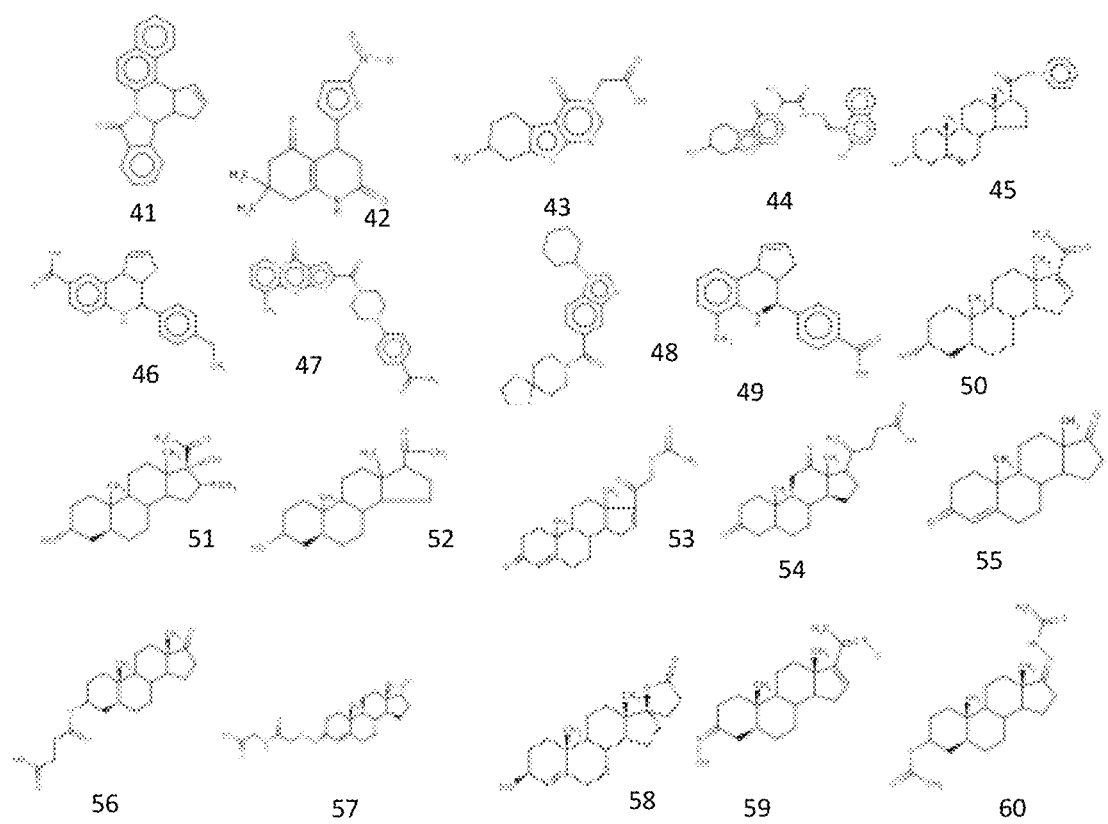
Figure 1D:
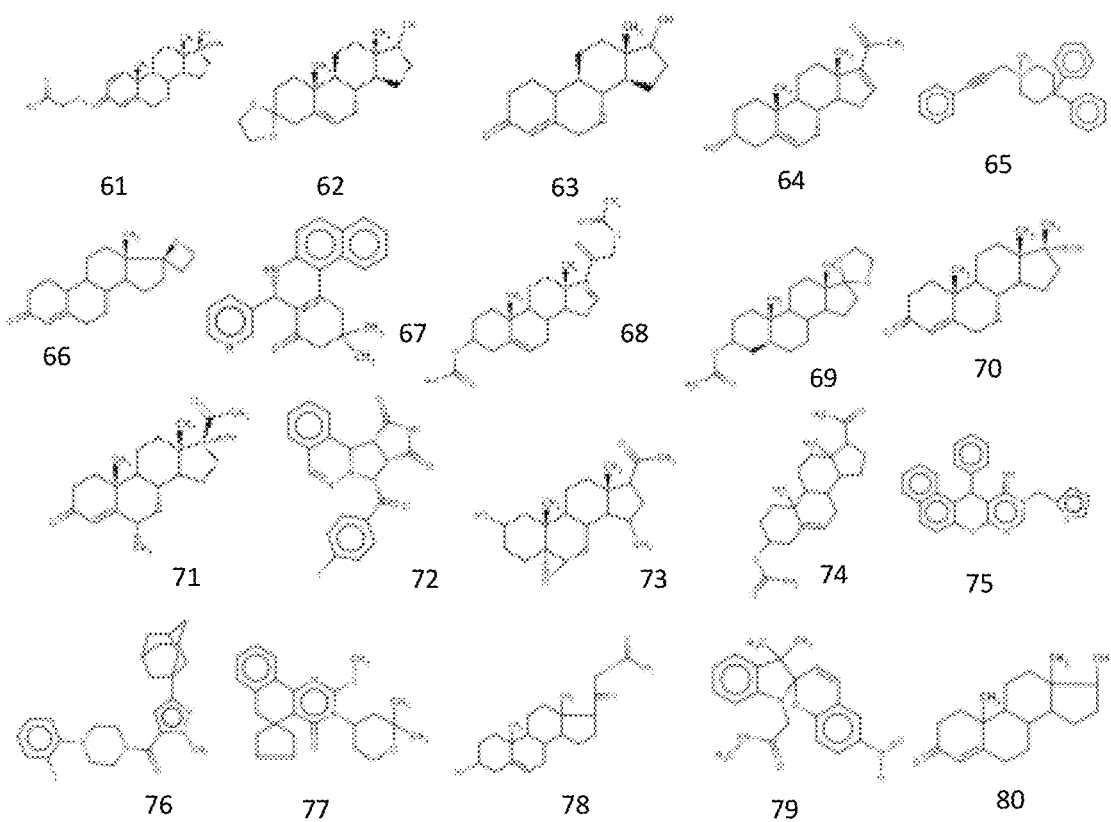
Figure 1E:
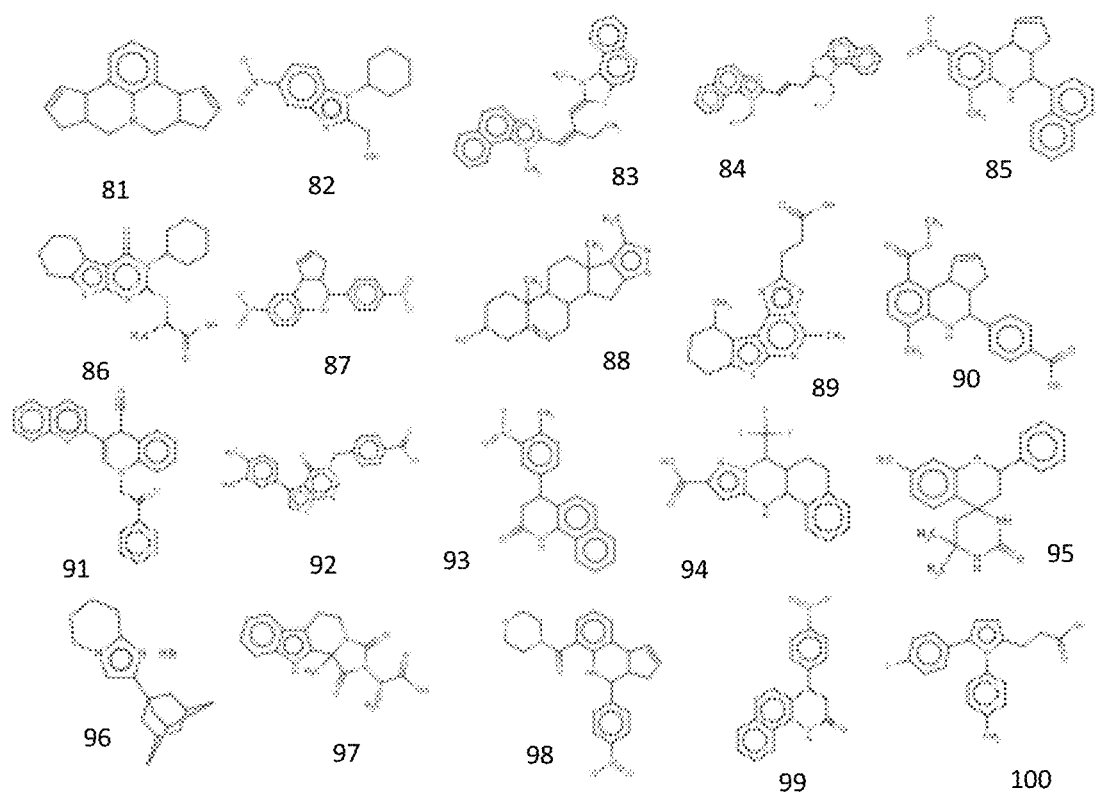
Figure 1F:
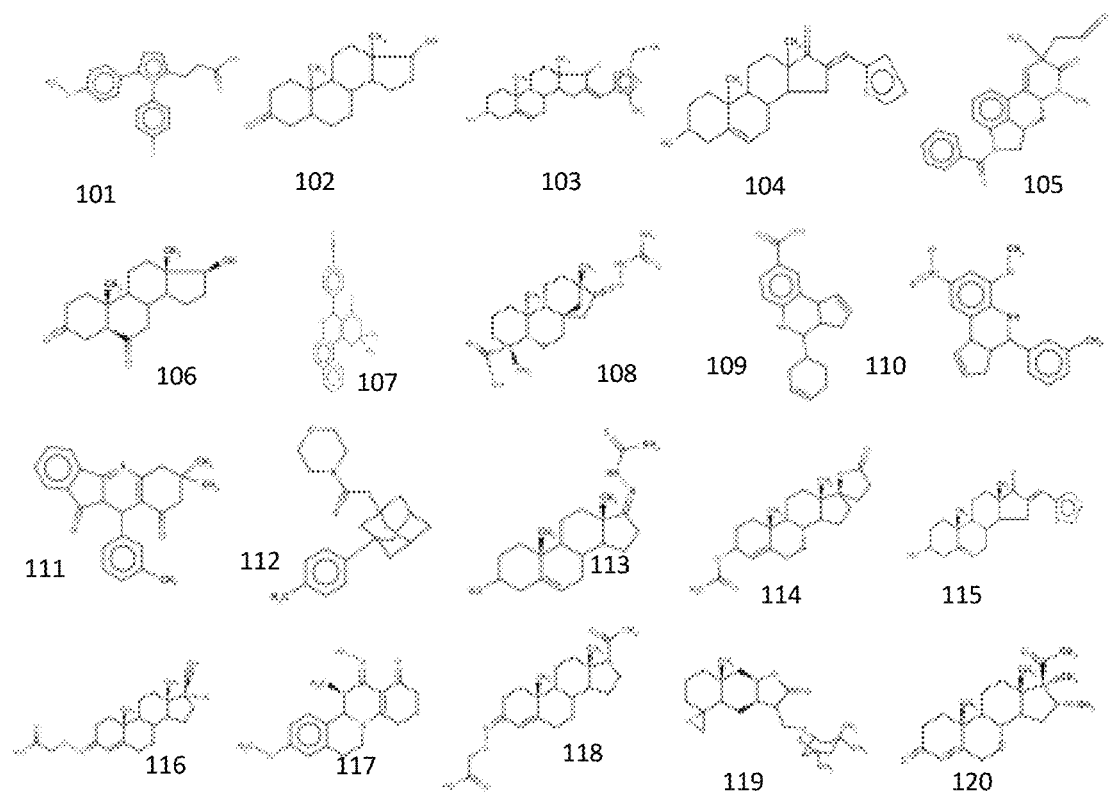
Figure 1G:
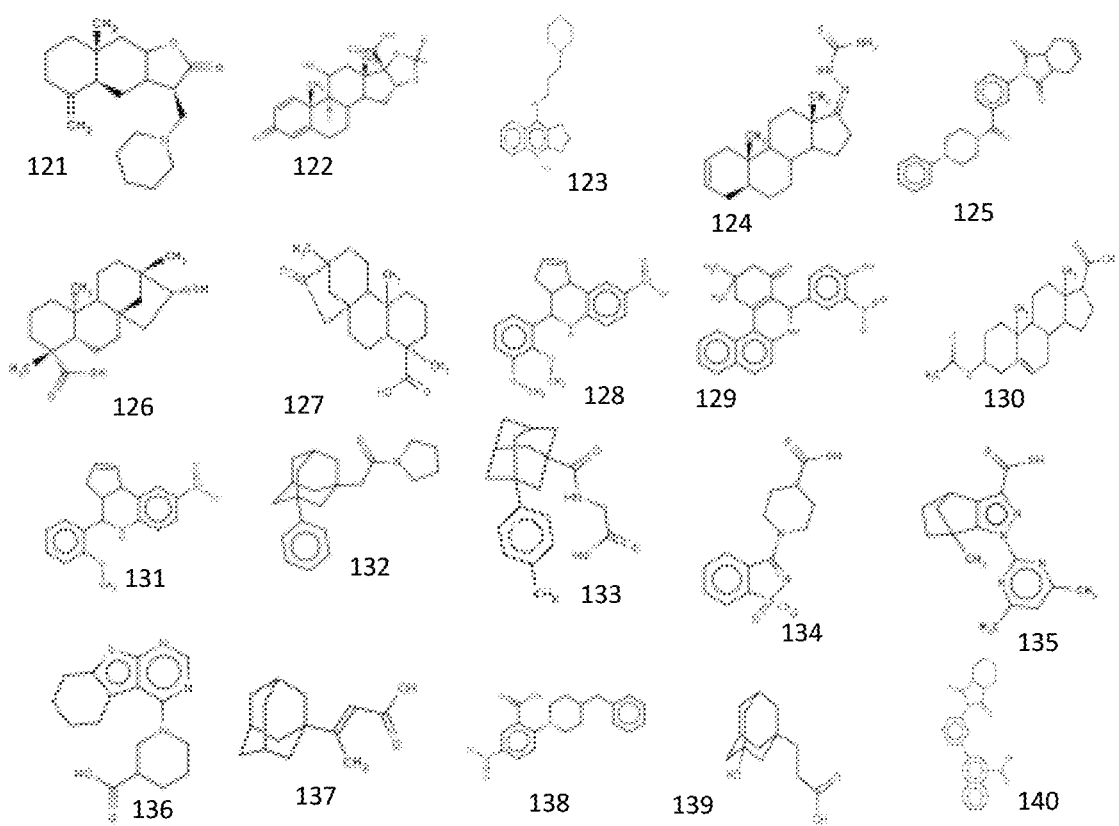
Figure 1H:
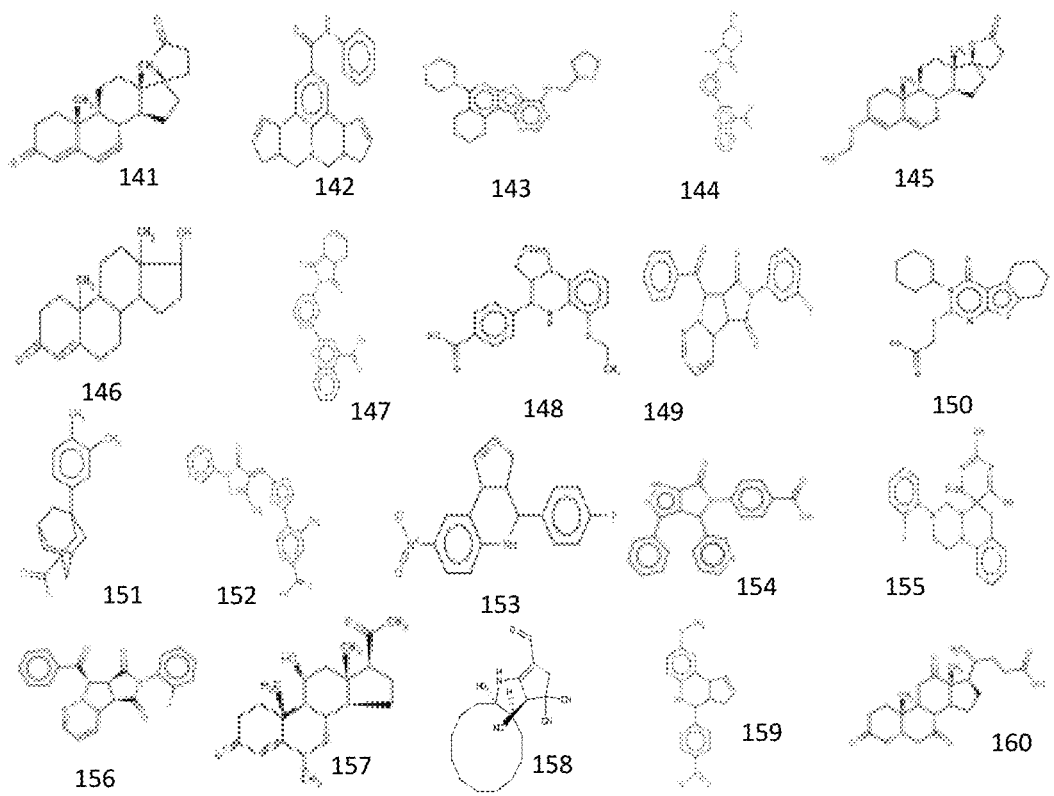

Human Noroviruses (NoVs) are believed to replicate and cause disease in the intestinal tract. NoVs are non-enveloped viruses that are encapsulated by an icosahedral protein capsid comprising 180 copies of the single major structural protein, the capsid protein (VP1). Based on its structural features, the capsid protein may be divided into two major domains, the shell (S) and the protruding (P) domains, each forming the interior shell and the arch-like protrusions of NoV capsid, respectively. The P domain can be further divided into P1 and P2 subdomains, constituting the leg and the head of the arch-shaped P dimer, respectively [4]. The P domain plays an important role in host immune response and receptor recognition. Heterologous expression of the P domain in E. coli forms P dimers [4] that is structurally and functionally indistinguishable from the authentic P dimers of viruses [5-11], providing a simple model for study of NoV-host interaction [12-17]. In addition, production of P domain with end modifications can also form 24mer P particles

[12,14,15] and 12mer small P particle [13], which contain 12 and 6 copies of P dimers, respectively.

Noroviruses recognize human histo-blood group antigens (HBGAs) as receptors or attachment factors, which play an important role in host susceptibility to Norovirus infection [18-21]. HBGAs are complex carbohydrates that are presented abundantly on the surface of mucosal epithelia of gastrointestinal track, where they may function as anchors for NoVs to initiate an infection. Human HBGAs are highly polymorphic that contain three major families, the ABO, secretor and Lewis families. Human Noroviruses are also highly diverse and multiple receptor binding patterns with different ABO, secretor and Lewis antigens have been described. The HBGA interacting sites have been mapped to the P domain of Norovirus capsid [4,12-14,22]. Further X-ray crystallography of the recombinant P dimers of a number of human Noroviruses representing different HBGA binding patterns in complex with different HBGA oligosaccharides has been resolved which provided valuable structural basis of the HBGA-NoV interactions [5-10]. The attachment through the HBGA receptors on the intestinal epithelia is believed to be a necessary first step of infection, and an inhibition of this step can be an effective treatment of the disease. This treatment may benefit patients who already contracted the infection, and may be particularly important for outbreak control of Norovirus gastroenteritis. Administration of a high concentration of an inhibiting compound to all individuals who at risk in an outbreak immediately after the identification of the index patient (prophylactic therapy) may provide effective protection and significant control over the outbreak.

Noroviruses require only 10-100 infectious particles to initiate an infection and the viral inoculums may not be high titered under a natural condition because Noroviruses are transmitted by person-to-person contact, or by contaminated surface, food, or water. Thus, it may not be difficult for the inhibiting compounds to compete with the intake virus that might initiate the infection. The treatment may also reduce the symptoms of a patient even after the onset of disease if the administered compound(s) have sufficient affinity to compete with the virus for the HBGA receptors. Furthermore, if the inhibiting compounds are highly stable and remain functional, they may further reduce the infection by blocking the progeny viruses for subsequent cycles of replication.

The human intestinal tract contains a large surface area and the HBGA receptors are highly abundant on the mucosal surface, making it difficult for a compound to block all receptor binding sites on the surfaces. The human intestinal tract is a complicated environment that contains various components (salts, bile acids, enzymes, digested and undigested food and nutrients) and extreme chemo-physical conditions that could interfere with the compound functioning as an antiviral against Noroviruses. Therefore, in addition to high affinity and high specificity, an inhibiting compound should ideally survive in the intestinal tract and have good biosafety in the host.

The HBGA binding interfaces are located at the top of the P dimer, corresponding to the outermost surface of the capsid. The carbohydrate binding pockets involve several scattered amino acid residues in the P domain that form extensive hydrogen bond network with individual saccharides, and thus stabilizing the binding of HBGAs to the capsid protein. Structure-based mutagenesis followed by functional analyses has confirmed the observed HBGA binding sites [7, 15, 16]. This detailed structural information of NoV-HBGA interactions opens a way to a new strategy for antiviral development through Computer-Aided Drug Design (CADD), while the established biological assays of NoV P dimer-HBGA interaction provide a convenient approach for validation of hit compounds identified by CADD.

CADD is a common approach in drug discovery that typically involves following major steps: 1) construction and validation of computational models of the target protein based on its crystal structures with known functional (HBGA binding) sites; 2) virtual high throughput screening (VHTS) of a large number of chemical compounds to identify candidate inhibitors (hit compounds) that are predicted to bind to the functional site of the protein with sufficiently high affinity; and 3) validation of the candidate inhibitors through biological and biochemical assays. Further development of promising candidate inhibitors includes assessment of their toxicity, pharmacokinetic and rational re-design based on structures of individual candidates, with the goals of improving efficacy while lowering toxicity and other undesired properties.

VHTS has been widely used for candidate compound discovery due to an advantage in elimination of undesired molecules from compound libraries, so that the cost and labor can be greatly reduced in a drug discovery project. A number of public compound libraries are currently available for VHTS, including Zinc (http://zinc.docking.org/) [23], NCI (http://cactus.nci.nih.gov/download/nci/), UC Irwine Chem B D [24], and Ligand-Depot [25]. VHTS of large databases of chemical compounds has been repeatedly shown to successfully identify hit compounds that can effectively inhibit the function of a given protein [26-29].

DEFINITIONS

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

Compositions

In one aspect, compositions useful for treatment and/or prevention of a NoV infection in a host are disclosed. The host may be a mammal, for example a human. In one aspect, the composition may comprise a compound comprising a cyclopenta alpha dimethyl phenanthren structure and a pharmaceutically acceptable carrier, or excipient.

In one aspect, the composition may comprise a medicament or pharmaceutical composition comprising an active compound selected from any one of the compounds listed in FIG. 1 and/or Table I, or a combination thereof, wherein the compound is a Norovirus binding-inhibiting compound, and a pharmaceutically acceptable carrier or excipient.

In one aspect, the composition may comprise a medicament or pharmaceutical composition comprising an active compound selected from any one of the compounds listed in Table 1, or a combination thereof, wherein the compound is a Norovirus binding-inhibiting compound, and a pharmaceutically acceptable carrier or excipient.

TABLE 1

Compounds 1-21.

| Activity (IC$_{50}$) | Structures |
| --- | --- |
| 1-10 μM | Compound 1 ZINC04041115      Compound 2 ZINC05260830 |

TABLE 1-continued

Compounds 1-21.

| Activity (IC$_{50}$) | Structures |
|---|---|

Compound 3
ZINC05223451

Compound 4
ZINC04831336

Compound 5
ZINC04026813

10-20 μM

Compound 6
ZINC04095376

Compound 7
ZINC04725822

TABLE 1-continued

Compounds 1-21.

| Activity (IC$_{50}$) | Structures |
|---|---|
|  | Compound 8 ZINC00128665 — Compound 9 ZINC06166484 |
|  | Compound 10 ZINC04084183 |
| 20-40 μM | Compound 11 ZINC04081424 — Compound 12 ZINC04450155 |
|  | Compound 13 ZINC00124088 — Compound 14 ZINC00968234 |

TABLE 1-continued

Compounds 1-21.

Activity (IC$_{50}$) | Structures

Compound 15
ZINC04062835

Compound 16
ZINC00652738

Compound 17
sZINC00181174

Compound 18
ZINC04014899

Compound 19
ZINC03814360

Compound 20
ZINC04298453

Compound 21 Dimethyl cyclopenta-α-phenanthren:

In one aspect, the composition may comprise a medicament or pharmaceutical composition comprising an active compound selected from any one of the compounds 1 through 5, or a combination thereof, wherein the compound is a Norovirus binding-inhibiting compound, and a pharmaceutically acceptable diluent, carrier or excipient.

Typically the composition comprises at least one binding-inhibiting compound that can prevent a Norovirus from binding with at least one histo-blood group antigen. Typically the composition comprises at least one binding-inhibiting compound that can prevent a Norovirus from binding with an H epitope, and/or with an A epitope, and/or with a B epitope, and/or with a Lewis epitope. An effective composition comprises a plurality of binding-inhibiting compound that can bind with any type of Norovirus regardless of the Norovirus binding pattern to the histo-blood group antigens.

The amount of the binding-inhibiting compound in the composition may be from about 1,000 to about 100,000 units per dose, where a unit defines the amount of the binding-inhibiting compound to bind with a single Norovirus particle.

Non-limiting examples of suitable pharmaceutically acceptable diluents and carriers include phosphate buffered saline solutions, water, emulsions including oil/water emulsions, various types of wetting agents such as detergents, and sterile solutions. Compositions comprising such carriers can be formulated by well known conventional methods. Compositions can also comprise liquid or viscous compositions that can coat and/or line the surface of the GI tract, thereby placing the active compounds in direct proximity with the epithelial cells.

Compounds, or mixtures of compounds described herein, can be formulated into pharmaceutical composition comprising a pharmaceutically acceptable carrier and other excipients as apparent to the skilled worker. Such composition can additionally contain effective amounts of other compounds, especially for the treatment of conditions, diseases, and/or disorders described herein.

Some embodiments comprise the administration of a pharmaceutically effective quantity of active agent or its pharmaceutically acceptable salts or esters, active agent analogs or their pharmaceutically acceptable salts or esters, or a combination thereof.

The compositions and preparations may contain at least 0.1% of active agent. The percentage of the compositions and preparations can, of course, be varied, and can contain between about 2% and 60% of the weight of the amount administered. The percentage of the compositions and preparations may contain between about 2, 5, 10, or 15% and 30, 35, 40, 45, 50, 55, or 60% of the weight of the amount administered. The amount of active compounds in such pharmaceutically useful compositions and preparations is such that a suitable dosage will be obtained.

The disclosed active agents may form salts. Reference to a compound of the active agent herein is understood to include reference to salts thereof, unless otherwise indicated. The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") can be formed and are included within the term "salt(s)" as used herein. Pharmaceutically acceptable (e.g., non-toxic, physiologically acceptable) salts are preferred, although other salts are also useful, e.g., in isolation or purification steps, which can be employed during preparation. Salts of the compounds of the active agent can be formed, for example, by reacting a compound of the active agent with an amount of acid or base, such as an equivalent amount, in a medium such as one in which the salt precipitates or in an aqueous medium followed by lyophilization.

Pharmaceutically acceptable salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like.

The compounds can be formulated in various forms, including solid and liquid forms, such as tablets, gel, syrup, powder, aerosol, etc.

The compositions may contain physiologically acceptable diluents, fillers, lubricants, excipients, solvents, binders, stabilizers, and the like. Diluents that can be used in the compositions include but are not limited to dicalcium phosphate, calcium sulphate, lactose, cellulose, kaolin, mannitol, sodium chloride, dry starch, powdered sugar and for prolonged release tablet-hydroxy propyl methyl cellulose (HPMC). The binders that can be used in the compositions include but are not limited to starch, gelatin and fillers such as sucrose, glucose, dextrose and lactose.

Natural and synthetic gums that can be used in the compositions include but are not limited to sodium alginate, ghatti gum, carboxymethyl cellulose, methyl cellulose, polyvinyl pyrrolidone and veegum. Excipients that can be used in the compositions include but are not limited to microcrystalline cellulose, calcium sulfate, dicalcium phosphate, starch, magnesium stearate, lactose, and sucrose. Stabilizers that can be used include but are not limited to polysaccharides such as acacia, agar, alginic acid, guar gum and tragacanth, amphotsics such as gelatin and synthetic and semi-synthetic polymers such as carbomer resins, cellulose ethers and carboxymethyl chitin.

Solvents that can be used include but are not limited to Ringers solution, water, distilled water, dimethyl sulfoxide to 50% in water, propylene glycol (neat or in water), phosphate buffered saline, balanced salt solution, glycol and other conventional fluids.

The dosages and dosage regimen in which the compounds are administered will vary according to the dosage form, mode of administration, the condition being treated and particulars of the patient being treated. Accordingly, optimal therapeutic concentrations will be best determined at the time and place through routine experimentation.

The compounds may also be used enterally. Orally, the compounds may be administered at the rate of 100 µg to 100 mg per day per kg of body weight. Orally, the compounds may be suitably administered at the rate of about 100, 150, 200, 250, 300, 350, 400, 450, or 500 µg to about 1, 5, 10, 25, 50, 75, 100 mg per day per kg of body weight. The required dose can be administered in one or more portions. For oral administration, suitable forms are, for example, tablets, gel, aerosols, pills, dragees, syrups, suspensions, emulsions, solutions, powders and granules; one method of administration includes using a suitable form containing from 1 mg to about 500 mg of active substance. In one aspect, administration may comprise using a suitable form containing from about 1, 2, 5, 10, 25, or 50 mg to about 100, 200, 300, 400, 500 mg of active substance.

The compounds may also be administered parenterally in the form of solutions or suspensions for intravenous or intramuscular perfusions or injections. In that case, the compounds may be administered at the rate of about 10 µg to 10 mg per day per kg of body weight; one method of administration may consist of using solutions or suspensions containing approximately from 0.01 mg to 1 mg of active substance per ml. The compounds may be administered at the rate of about 10, 20, 30, 40, 50, 60, 70, 80, 90, or 100 µg to 1, 2, 3, 4, 5, 6, 7, 8, 9, or 10 mg per day per kg of body weight; in one aspect, solutions or suspensions containing approximately from 0.01, 0.02, 0.03, 0.04, or 0.5 mg to 0.1, 0.2, 0.3, 0.4, 0.5, 0.6, 0.7, 0.8, 0.9, or 1 mg of active substance per ml may be used.

The compounds can be used in a substantially similar manner to other known anti-cancer agents for treating (both chemopreventively and therapeutically) various cancers. For the anti-cancer dose to be administered, whether a single dose, multiple dose, or a daily dose, will of course vary with the particular compound employed because of the varying potency of the compound, the chosen route of administration, the size of the recipient, the type of cancer, and the nature of the patient's condition. The dosage to be administered is not subject to definite bounds, but it will usually be an effective amount, or the equivalent on a molar basis of the pharmacologically active free form produced from a dosage formulation upon the metabolic release of the active drug to achieve its desired pharmacological and physiological effects. For example, an oncologist skilled in the art of cancer treatment will be able to ascertain, without undue experimentation, appropriate protocols for the effective administration of the compounds related to cancer therapy, such as by referring to the earlier published studies on compounds found to have anti-cancer properties.

The active compounds and/or pharmaceutical compositions of the embodiments disclosed herein can be administered according to various routes, such as by injection, for example local or systemic injection(s). Intratumoral injections may be used for treating existing cancers. Other administration routes can be used as well, such as intramuscular, intravenous, intradermic, subcutaneous, etc. Furthermore, repeated injections can be performed, if needed, although it is believed that limited injections will be needed in view of the efficacy of the compounds.

For ex vivo administration, the active agent can be administered by any standard method that would maintain viability of the cells, such as by adding it to culture medium (appropriate for the target cells) and adding this medium directly to the cells. As is known in the art, any medium used in this method can be aqueous and non-toxic so as not to render the cells non-viable. In addition, it can contain standard nutrients for maintaining viability of cells, if desired. For in vivo administration, the complex can be added to, for example, to a pharmaceutically acceptable carrier, e.g., saline and buffered saline, and administered by any of several means known in the art. Examples of administration include parenteral administration, e.g., by intravenous injection including regional perfusion through a blood vessel supplying the tissues(s) or organ(s) having the target cell(s), or by inhalation of an aerosol, subcutaneous or intramuscular injection, topical administration such as to skin wounds and lesions, direct transfection into, e.g., bone marrow cells prepared for transplantation and subsequent transplantation into the subject, and direct transfection into an organ that is subsequently transplanted into the subject. Further administration methods include oral administration, particularly when the active agent is encapsulated, or rectal administration, particularly when the active agent is in suppository form.

It is contemplated that such target cells can be located within a subject or human patient, in which case a safe and effective amount of the active agent, in pharmacologically acceptable form, would be administered to the patient. Generally speaking, it is contemplated that useful pharmaceutical compositions may include the selected active compound derivative in a convenient amount, e.g., from about 0.001% to about 10% (w/w) that is diluted in a pharmacologically or physiologically acceptable carrier, such as, for example, phosphate buffered saline. The route of administration and ultimate amount of material that is administered to the subject under such circumstances will depend upon the intended application and will be apparent to those of skill in the art in light of the examples which follow.

Any composition chosen should be of low or non-toxicity to the cell. Toxicity for any given compound can vary with the concentration of compound used. It is also beneficial if the compound chosen is metabolized or eliminated by the body and if this metabolism or elimination is done in a manner that will not be harmfully toxic.

The compound may be administered such that a therapeutically effective concentration of the compound is in contact with the affected cells of the body. The dose administered to a subject, particularly a human, may be sufficient to effect a therapeutic response in the subject over a reasonable period of time. The dose may be determined by the strength of the particular compound employed and the condition of the subject, as well as the body weight of the subject to be treated. The existence, nature, and extent of any adverse side effects that might accompany the administration of a particular compound also will determine the size of the dose and the particular route of administration employed with a particular patient. In general, the compounds may be therapeutically effective at low doses. The generally useful dose range may be from about 0.001 mM, or less, to about 100 mM, or more. The effective dose range may be from about 0.01, 0.05, 0.1, 0.5, 0.6, 0.7, 0.8, or 0.9 mM, to about 1, 2, 3, 4, 5, 6, 7, 8, 9, or 10 mM. Accordingly, the compounds may be generally administered in low doses.

The pharmaceutical composition may further comprise a pharmaceutically acceptable carrier. The resulting preparation may incorporate, if necessary, one or more solubilizing agent, buffers, preservatives, colorants, perfumes, flavorings and the like that are widely used in the field of pharmaceutical preparation.

The proportion of the active ingredient to be contained in the disclosed compositions may be determined by one of ordinary skill in the art using art recognized methods.

The disclosed compounds may be formulated into a dosage form selected from the group consisting of tablets, capsules, granules, pills, injections, solutions, emulsions, suspensions, and syrups. The form and administration route for the pharmaceutical composition are not limited and can be suitably selected. For example, tablets, capsules, granules, pills, syrups, solutions, emulsions, and suspensions may be administered orally. Additionally, injections (e.g. subcutaneous, intravenous, intramuscular, and intraperitoneal) may be administered intravenously either singly or in combination with a conventional replenisher containing glucose, amino acid and/or the like, or may be singly administered intramuscularly, intracutaneously, subcutaneously and/or intraperitoneally.

The disclosed compositions may be prepared according to a method known in the pharmaceutical field of this kind using a pharmaceutically acceptable carrier. For example, oral forms such as tablets, capsules, granules, pills and the like are prepared according to known methods using excipients such as saccharose, lactose, glucose, starch, mannitol and the like; binders such as syrup, gum arabic, sorbitol, tragacanth, methylcellulose, polyvinylpyrrolidone and the like; disintegrates such as starch, carboxymethylcellulose or the calcium salt thereof, microcrystalline cellulose, polyethylene glycol and the like; lubricants such as talc, magnesium stearate, calcium stearate, silica and the like; and wetting agents such as sodium laurate, glycerol and the like.

Injections, solutions, emulsions, suspensions, syrups and the like may be prepared according to a known method suitably using solvents for dissolving the active ingredient, such as ethyl alcohol, isopropyl alcohol, propylene glycol, 1,3-butylene glycol, polyethylene glycol, sesame oil and the like; surfactants such as sorbitan fatty acid ester, polyoxyethylenesorbitan fatty acid ester, polyoxyethylene fatty acid ester, polyoxyethylene of hydrogenated castor oil, lecithin and the like; suspending agents such as cellulose derivatives including carboxymethylcellulose sodium, methylcellulose and the like, natural gums including tragacanth, gum arabic and the like; and preservatives such as parahydroxybenzoic acid esters, benzalkonium chloride, sorbic acid salts and the like.

The compounds can be administered orally, topically, parenterally, by inhalation or spray, vaginally, rectally or sublingually in dosage unit formulations. The term "administration by injection" includes but is not limited to: intravenous, intraarticular, intramuscular, subcutaneous and parenteral injections, as well as use of infusion techniques. Dermal administration can include topical application or transdermal administration. One or more compounds can be present in association with one or more non-toxic pharmaceutically acceptable carriers and if desired other active ingredients.

Compositions intended for oral use can be prepared according to any suitable method known to the art for the manufacture of pharmaceutical compositions. Such compositions can contain one or more agents selected from the group consisting of diluents, sweetening agents, flavoring agents, coloring agents and preserving agents in order to provide palatable preparations. Tablets contain the active ingredient in admixture with non-toxic pharmaceutically acceptable excipients that are suitable for the manufacture of tablets. These excipients can be, for example, inert diluents, such as calcium carbonate, sodium carbonate, lactose, calcium phosphate or sodium phosphate; granulating and disintegrating agents, for example, corn starch, or alginic acid; and binding agents, for example magnesium stearate, stearic acid or talc. The tablets can be uncoated or they can be coated by known techniques to delay disintegration and adsorption in the gastrointestinal tract and thereby provide a sustained action over a longer period. For example, a time delay material such as glyceryl monostearate or glyceryl distearate can be employed. These compounds can also be prepared in solid, rapidly released form.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions containing the active materials in admixture with excipients suitable for the manufacture of aqueous suspensions can also be used. Such excipients are suspending agents, for example sodium carboxymethylcellulose, methylcellulose, hydroxypropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethylene oxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, can also be present.

The compounds can also be in the form of non-aqueous liquid formulations, e.g., oily suspensions which can be formulated by suspending the active ingredients in a vegetable oil, for example arachis oil, olive oil, sesame oil or peanut oil, or in a mineral oil such as liquid paraffin. The oily suspensions can contain a thickening agent, for example beeswax, hard paraffin or cetyl alcohol. Sweetening agents such as those set forth above, and flavoring agents can be added to provide palatable oral preparations. These compositions can be preserved by the addition of an anti-oxidant such as ascorbic acid.

Compounds may also be administrated transdermally using methods known to those skilled in the art. For example, a solution or suspension of an active agent in a suitable volatile solvent optionally containing penetration enhancing agents can be combined with additional additives known to those skilled in the art, such as matrix materials and bacteriocides. After sterilization, the resulting mixture can be formulated following known procedures into dosage forms. In addition, on treatment with emulsifying agents and water, a solution or suspension of an active agent can be formulated into a lotion or salve.

Suitable solvents for processing transdermal delivery systems are known to those skilled in the art, and include lower alcohols such as ethanol or isopropyl alcohol, lower ketones such as acetone, lower carboxylic acid esters such as ethyl acetate, polar ethers such as tetrahydrofuran, lower hydrocarbons such as hexane, cyclohexane or benzene, or halogenated hydrocarbons such as dichloromethane, chloroform, trichlorotrifluoroethane, or trichlorofluoroethane. Suitable solvents can also include mixtures of one or more materials selected from lower alcohols, lower ketones, lower carboxylic acid esters, polar ethers, lower hydrocarbons, halogenated hydrocarbons.

Suitable penetration enhancing materials for transdermal delivery system are known to those skilled in the art, and include, for example, monohydroxy or polyhydroxy alcohols such as ethanol, propylene glycol or benzyl alcohol, saturated or unsaturated C8-C18 fatty alcohols such as lauryl alcohol or cetyl alcohol, saturated or unsaturated C8-C18 fatty acids such as stearic acid, saturated or unsaturated fatty esters with up to 24 carbons such as methyl, ethyl, propyl, isopropyl, n-butyl, sec-butyl, isobutyl, tertbutyl or monoglycerin esters of acetic acid, capronic acid, lauric acid, myristinic acid, stearic acid, or palmitic acid, or diesters of saturated or unsaturated dicarboxylic acids with a total of up to about 24 carbons such as diisopropyl adipate, diisobutyl adipate, diisopropyl sebacate, diisopropyl maleate, or diisopropyl fumarate. Additional penetration enhancing materials include phosphatidyl derivatives such as lecithin or cephalin, terpenes, amides, ketones, ureas and their derivatives, and ethers such as dimethyl isosorbid and diethyleneglycol monoethyl ether. Suitable penetration enhancing formulations can also include mixtures of one or more materials selected from monohydroxy or polyhydroxy alcohols, saturated or unsaturated C8-C18 fatty alcohols, saturated or unsaturated C8-C18 fatty acids, saturated or unsaturated fatty esters with up to 24 carbons, diesters of saturated or unsaturated discarboxylic acids with a total of up to 24 carbons, phosphatidyl derivatives, terpenes, amides, ketones, ureas and their derivatives, and ethers.

Suitable binding materials for transdermal delivery systems are known to those skilled in the art and include polyacrylates, silicones, polyurethanes, block polymers, styrenebutadiene copolymers, and natural and synthetic rubbers. Cellulose ethers, derivatized polyethylenes, and silicates can also be used as matrix components. Additional additives, such as viscous resins or oils can be added to increase the viscosity of the matrix.

Pharmaceutical compositions may also be in the form of oil-in-water emulsions. The oil phase can be a vegetable oil, for example olive oil or arachis oil, or a mineral oil, for example, liquid paraffin or mixtures of these. Suitable emulsifying agents can be naturally-occurring gums, for example, gum acacia or gum tragacanth, naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions can also contain sweetening and flavoring agents. Syrups and elixirs can be formulated with sweetening agents, for example glycerol, propylene glycol, sorbitol or sucrose. Such formulations can also contain a demulcent, a preservative and flavoring and coloring agents.

The compounds can also be administered in the form of suppositories for rectal or vaginal administration of the drug. These compositions can be prepared by mixing the drug with a suitable nonirritating excipient which is solid at ordinary temperatures but liquid at the rectal temperature or vaginal temperature and will therefore melt in the rectum or vagina to release the drug. Such materials include cocoa butter and polyethylene glycols.

It will be appreciated by those skilled in the art that the particular method of administration will depend on a variety of factors, all of which are considered routinely when administering therapeutics. It will also be understood, however, that the specific dose level for any given patient will depend upon a variety of factors, including, the activity of the specific compound employed, the age of the patient, the body weight of the patient, the general health of the patient, the gender of the patient, the diet of the patient, time of administration, route of administration, rate of excretion, drug combinations, and the severity of the condition undergoing therapy. It will be further appreciated by one skilled in the art that the optimal course of treatment, i.e., the mode of treatment and the daily number of doses of an active agent or a pharmaceutically acceptable salt thereof given for a defined number of days, can be ascertained by those skilled in the art using conventional treatment tests.

Methods of Treatment

In one aspect, a method for treating and/or preventing an infection of a host, typically a mammal, by a Norovirus, by administering to the host an effective preventative amount of the binding-inhibiting compound that inhibits binding of at least one Norovirus to a native histo blood group antigen of the host, is disclosed.

In one aspect, a method for treating and/or preventing an active infection of a host by a Norovirus, by administering to the host an effective treatment amount of the binding-inhibiting compound that inhibits binding of the infecting Norovirus to the histo blood group antigen of the host is disclosed.

When an outbreak of a Norovirus occurs, the time to isolate and detect the specific strain of Norovirus for pinpoint treatment can delay administration of treatment or prevention compositions to a population of infected or susceptible persons. A combination of compounds in a single medicament or pharmaceutical composition that can singularly or jointly bind with any strain of Norovirus, would be helpful to ensure effective treatment or prevention of infection, regardless of the particular strain(s) of Norovirus involved.

The effective prevention amount of the prevention compound may comprise an amount sufficient to bind most or all of the Norovirus capsids or particles that are present in the gastrointestinal system of a host who had consumed a food, water, or other source contaminated by the Norovirus. Ordinarily, the contaminating amounts of Norovirus would be very low. The amount of the binding-inhibiting compound to be consumed for prevention or treatment typically ranges from about 100 to about 10,000 units per dose, or from about 1,000 to about 10,000 units per dose, where a unit defines the amount of the binding-inhibiting compound to bind with a single virus particle. In one aspect, a dose of the medicament comprising the binding-inhibiting compound may be consumed by the host just prior to, while, or just after, consuming a food or water suspected of being contaminated with a Norovirus.

The effective treatment amount of the binding-inhibiting compound may comprise an amount sufficient to bind most or all of the Norovirus capsids or particles that are progeny from those infected within the epithelial cells of the gastrointestinal system of the host. Ordinarily, these amounts or levels of Norovirus are high compared to the amount of Norovirus found in the contaminated water or food. The amount of the binding-inhibiting compound to be consumed will typically range from about 1,000 to about 100,000 units per dose, or from about 10,000 to about 100,000 units per dose, where a unit defines the amount of the compound to bind with a single Norovirus particle. In an aspect, a dose of the medicament comprising the binding-inhibiting compound may be consumed by the host periodically until the symptoms of the infection have dissipated and stopped. Since any consumed compound would pass through the gastrointestinal system in the ordinary course, the periodic dosage may be administered about every 1 to 4 hours.

The compounds may be non-toxic and have no adverse side effects on the host, including non-binding or associating with other antigens in the host's system. This can be demonstrated based on in vitro experiments.

Example 1

Inhibitors of HBGA binding to NoVs as potential antivirals against NoVs through a CADD procedure are disclosed herein. The crystal structures of the VA387 (a member of the predominant GII.4 NoVs) P dimer interacting with HBGA were employed to construct computer models for VHTS. After validations of the models by virtual docking simulation using the type A- and B-trisaccharides as ligands, VTHS of a large drug-like compound library was performed, resulting in 255 hit compounds. A total of 160 compounds of the compounds were further tested by biological assays and five revealed strong blocking activity on P dimer-HBGA interaction with an $IC_{50}$<10 μM. The results suggest that the CADD approach can facilitate the development of antivirals against human NoVs and the five highly active compounds could become a basis for developing promising drug candidates against NoVs.

Materials and Methods

Computer Models of P Dimers and Oligosaccharides.

The two PDB files revealing the crystal structures of the P dimers of VA387 (a predominant GII.4 NoVs) in complex with A (2OBS) and B (2OBT) HBGA oligosaccharides, respectively [6], were downloaded from Protein Data Bank (PDB, http://www.pdb.org). The protein structures with removal of the HBGA ligands were used as model of P dimer, while the extracted HBGA structures were used as models of A and B trisaccharides. Preparation of the HBGA model included specifying rotatable bonds, assigning partial charges, and preparing grid boxes for docking simulations, which was performed using AutoDock package. Preparation of the P dimer model included adding polar hydrogens, checking missing atoms, assigning charges and solvation parameters. Information of HBGA oligosaccharides interacting with the amino acids that constitute the HBGA binding sites were used to set parameters for molecular docking.

Docking Simulation.

Re-docking simulations were used for validation of the structural models and docking protocols. The results obtained by docking the native ligands (A and B trisaccharides) to the P dimer were compared with the structural data on P dimer in complex with HBGAs [6]. Using AutoDock 3 package [30] a series of rigid (P dimer) body simulations were performed, followed by additional assessment of the results from "flexible ligand-flexible key binding residues of the P dimer" docking simulations. Rigid body docking was qualitatively consistent with flexible docking simulations, and able to reproduce experimentally observed conformations of the P dimer-HBGAs complexes. In particular, majority of over 200 different poses generated in repeated rigid body simulations were found to be in good agreement with experimental data. Grid boxes and grid densities for rigid body docking were optimized to provide sufficient accuracy and to cover the binding site(s) that might occur over the whole P dimer molecule (blind docking). Docked conformations of ligands were generated by AutoDock's Lamarckian genetic algorithm (GA) [31]. Docking parameters used for the simulations are listed in Table 3. Docking simulations and the VTHS (see below) were conducted on the Cincinnati Children's Hospital Medical Center's BMI computational cluster with over 200 processing cores (at least 2.4 GHz) running 64-bit SuSE Linux operating system.

TABLE 3

Parameters used for Docking Simulation

| Iteration Parameters | |
| --- | --- |
| Translation step | 2 Å |
| Quaternion step | 50° |
| Torsion step | 50° |
| Lamarckian Genetic Algorithm Parameters | |
| Number of Genetic Algorithm runs | 255 |
| Initial population size | 300 |
| Maximum number of energy evaluations | 2.5 million |
| Maximum number of generations | 35,000 |
| No. of top individuals that automatically survive | 1 |
| Rate of gene mutation | 0.02 |
| Rate of crossover | 0.8 |
| Number of generations for picking worst individual | 10 |
| Number of iterations of pseudo Solis and Wets local search | 300 |
| Number of consecutive successes before changing | 4 |
| Number of consecutive failures before changing | 4 |
| Probability of performing local search on an individual | 0.06 |
| Grid Parameters | |
| Grid Spacing | 0.375 Å |
| Number of grid points in x, y, and z directions | 78, 50, 45 |

VHTS of the Compound Library.

A subset of the public compound library ZINC, consisting of 2,066,906 drug-like compounds was downloaded from the ZINC database (http://zinc.docking.org/). In the initial stage of VTHS, these compounds were subjected to the automatic molecular docking using the "rigid P dimer-flexible ligand" approach and AutoDock ver. 3. The primary screening was done using coarse-level docking with limited sampling [26,32]. Compounds predicted to have <0.1 μM inhibition constant (Ki<$10^{-7}$) were subsequently subjected to a secondary round of screening with improved sampling. The protocol used for secondary screening (see Table 4) involved an increased number of overall simulation runs, increased number of energy evaluation, increased size of the GA population [33], and a finer grid resolution (decreased from 0.6 to 0.375 Ang).

TABLE 4

| | Primary | Secondary |
| --- | --- | --- |
| Iteration Parameters | | |
| Translation step | 2 Å | 2 Å |
| Quaternion step | 50° | 50° |
| Torsion step | 50° | 50° |
| Lamarckian Genetic Algorithm Parameters | | |
| Number of Genetic Algorithm runs | 10 | 100 |
| Initial population size | 50 | 500 |
| Maximum number of energy evaluations | 150,000 | 500,000 × torsion |
| Maximum number of generations | 27,000 | 27,000 |
| No. of top individuals that automatically survive | 1 | 1 |
| Rate of gene mutation | 0.02 | 0.02 |

TABLE 4-continued

|  | Primary | Secondary |
|---|---|---|
| Rate of crossover | 0.8 | 0.8 |
| Number of generations for picking worst individual | 10 | 10 |
| Number of iterations of pseudo Solis and Wets local search | 300 | 300 |
| Number of consecutive successes before changing | 4 | 4 |
| Number of consecutive failures before changing | 4 | 4 |
| Probability of performing local search on an individual | 0.06 | 0.06 |
| Grid Parameters | | |
| Grid Spacing | 0.6 Å | 0.375 Å |
| Grid points in x, y, and z directions | 49, 32, 29 | Split into two grids |

The identified top 255 hit compounds that were predicted to bind the HBGA binding site with better affinity than that of A and B oligosaccharides were selected for experimental validation. The bound P dimer structures of VA387 (2OBS) [6] with removal of the A-trisaccharides were used as model for the screening. The docking parameters for the primary VHTS were similar to those used in molecular docking (Table 2). To reduce the docking time, trivial parallelism of VHTS was exploited by performing docking simulations for subsets of compounds on individual computing nodes using a pipeline described in Biesiada et al [32].

Purchases of the Hit Compounds.

160 top hits (which were actually selected based on their availability from a somewhat larger initial set of 255 hit compounds obtained in virtual screening) were purchased from Molport (http://www.molport.com) supplied by Maybridg, TimTec, ChemBridge, Pharmeks, Specs, Otava, ChemDiv, InterBioScreen Ltd, Vitas-M Laboratory, Princeton Biomolecular Research and Enamine Ltd. The information including ZINC numbers and structures of the 160 chemicals are listed in FIG. 1. All compounds were dissolved at 100 µg/ml in PBS (pH 7.4) containing 1% DMSO as stock solutions.

Validation of Hit Compounds by NoV/HBGA Blocking Assays.

Saliva-based NoV-HBGA binding assays were performed as described previously using P dimers of VA387 (GII.4) as NoV surrogates and saliva samples and/or synthetic oligosaccharides as HBGA sources [4,34,35]. Briefly, synthetic oligosaccharides and/or boiled saliva samples with defined HBGAs phenotype were coated on 96-well microtiter plates, after blocking with nonfat milk, P dimer of VA387 were added. The bound P dimer was detected using a guinea pig antiserum against NoVs VLPs, followed by the addition of horseradish peroxidase (HRP)-conjugated goat anti-guinea pig IgG. The bound HRP conjugates were colorized by the TMB kit (Kirkegaard & Perry Laboratories), which was read an EIA spectrum reader (Tecan). The synthetic oligosaccharide-PAA conjugates (2 µg/ml, GlycoTech Corporation, Rockville, Md.) were captured to a microtiter plate through coated streptavidin (5 µg/ml) [36].

Blocking effects of the hit compounds were measured by a pre-incubation of the P dimers with the compounds at given concentrations for 30 min before the P dimers were added to the coated saliva samples or HBGA oligosaccharides in a binding assay [37]. The blocking activity of a compound was defined as its concentration yielding 50% inhibition ($IC_{50}$) in the binding assay. $IC_{50}$ calculation was performed using Probit regression analysis and correlation analysis between $IC_{50}$ and $K_i$ values was performed with nonparametric Spearman's r (two-tailed) by using SPSS statistical software version 13.0 (SPSS, Chicago, Ill.).

MTS Cytotoxicity Assay.

This assay was performed using CellTiter 96 aqueous nonradioactive cell proliferation kits (Promega, Madison, Wis.) as described elsewhere [36]. Briefly, HeLa and LLC-MK2 cells were seeded at $5 \times 10^4$ cells/ml onto a 96-well plate overnight. After an incubation with each compound at various concentrations for 3 days (the compound was added one time at the beginning of the incubation), the culture medium was replaced with fresh one with 100 µl of MTS-phenazine methosulfate/well. After a further incubation at 37° C. for 2 h, the color products of MTS were measured with a plate reader at 490 nm. The cytotoxicities of individual compounds were indicated by the decrease in cellular reduction of MTS into the colored product. The 50% cytotoxic concentrations ($CC_{50}$) were determined as the concentrations of the compounds that caused 50% inhibition of cell growth compared with that of control cells without a compound.

Results

Validation of the NoV Model and the Molecular Docking Protocol.

The crystal structures of NoV P dimers of VA387 (GII.4) with HBGA oligosaccharides (2OBS and 2OBT) [6] were used to build target structures for molecular docking and VTHS of the ZINC compound library. The models were first employed for validation by re-docking simulations using a type A trisaccharide as a ligand through software AutoDock 3 [30]. The vast majority of multiple poses of the A trisaccharide obtained in repeated simulations docked well to the experimentally mapped HBGA binding site of VA387 that was formed by seven amino acids: Ser343, Arg345, His347, Asp374, Gln376, Ser441 and Gly442. It was noted that some conformations of the A trisaccharide docked to an undefined nearby site. The predicted inhibition constants (IQ were relatively low (with the best predicted $K_i$ of about 1.6 µM), reflecting the nature of trisaccharide-protein interactions. Similar results were obtained when docking simulations were performed using the type B trisaccharide as a ligand (data not shown). Thus, these data are consistent with the crystal structures of the VA387 P dimer and provide validation of our computational models and molecular docking protocols.

VTHS and Laboratory Validation of Drug-Like Compounds Against NoV Binding to HBGAs.

Multistage screening of ~2.07 million compounds from the ZINC drug-like library has resulted in identification of 255 hit compounds with predicted inhibition constants Ki values less than 100 µM against VA387 binding to the A and/or B trisaccharides (FIG. 2A-H). A total of 160 compounds from the 255 compounds were purchased from several different companies based on their availability (see Materials and Methods) and tested by saliva-based blocking assays using VA387 P dimers as NoV surrogates and type A and B saliva samples as HBGA sources. Twenty compounds (12.5%) exhibited >50% inhibitory effects on the P dimer-saliva interactions at a concentration <40 µM. The specificities of the top 20 compounds were further studied by both saliva- and synthesized HBGA oligosaccharide-based blocking assays. Five of the 20 compounds showed strong inhibitions with $IC_{50}$, <10 µM; five others revealed good inhibitions with $IC_{50s}$ ranging from 10 to 20 µM, while the remaining ten compounds exhibited moderate inhibitions with $IC_{50s}$ ranging from 20-40 µM (Table 5).

TABLE 5

The basic features of the 20 most inhibitory lead-like compounds

| ZINC-codes | MW (Da) | Molecular Formula | Ki value (μM)[a] | IC50 (μM)[b] Saliva A | IC50 (μM)[b] Saliva B |
|---|---|---|---|---|---|
| ZINC04041115 | 344.49 | $C_{21}H_{32}N_2O_2$ | 0.64 | 2.38 ± 0.15 | 2.54 ± 0.21 |
| ZINC05260830 | 318.49 | $C_{21}H_{34}O_2$ | 1.25 | 2.90 ± 0.33 | 2.93 ± 0.18 |
| ZINC05223451 | 306.48 | $C_{20}H_{34}O_2$ | 1.14 | 3.37 ± 0.13 | 3.39 ± 0.24 |
| ZINC04831336 | 374.56 | $C_{24}H_{38}O_3$ | 0.36 | 7.63 ± 0.27 | 7.65 ± 0.33 |
| ZINC04026813 | 345.55 | $C_{20}H_{31}N_3S$ | 0.16 | 8.70 ± 1.03 | 8.97 ± 0.63 |
| ZINC04095376 | 307.35 | $C_{18}H_{17}N_3O_2$ | 3.25 | 12.6 ± 0.87 | 12.8 ± 0.64 |
| ZINC04725822 | 296.36 | $C_{18}H_{20}N_2O_2$ | 1.65 | 13.2 ± 1.04 | 13.1 ± 0.87 |
| ZINC00128665 | 277.36 | $C_{19}H_{19}NO$ | 1.58 | 14.1 ± 0.53 | 14.9 ± 0.71 |
| ZINC06166484 | 460.55 | $C_{25}H_{24}N_4O_3S$ | 1.16 | 17.0 ± 1.06 | 16.8 ± 0.87 |
| ZINC04084183 | 418.53 | $C_{23}H_{34}N_2O_5$ | 0.42 | 18.7 ± 0.35 | 18.6 ± 0.62 |
| ZINC04081424 | 344.49 | $C_{22}H_{32}O_3$ | 0.35 | 22.7 ± 1.36 | 23.7 ± 1.28 |
| ZINC04450155 | 323.35 | $C_{18}H_{17}N_3O_3$ | 7.77 | 24.2 ± 0.74 | 24.3 ± 0.87 |
| ZINC00124088 | 318.33 | $C_{19}H_{14}N_2O_3$ | 13.2 | 24.5 ± 0.98 | 26.3 ± 1.24 |
| ZINC00968234 | 314.46 | $C_{21}H_{30}O_2$ | 0.92 | 24.8 ± 2.02 | 25.1 ± 1.32 |
| ZINC04062835 | 274.4 | $C_{18}H_{26}O_2$ | 2.49 | 28.5 ± 1.54 | 29.4 ± 1.24 |
| ZINC00652738 | 374.51 | $C_{23}H_{34}O_4$ | 1.67 | 30.9 ± 1.04 | 30.1 ± 1.35 |
| ZINC00181174 | 332.35 | $C_{20}H_{16}N_2O_3$ | 3.85 | 33.5 ± 0.68 | 33.7 ± 1.27 |
| ZINC04014899 | 327.46 | $C_{21}H_{29}NO_2$ | 1.56 | 33.9 ± 1.67 | 34.5 ± 1.93 |
| ZINC03814360 | 290.44 | $C_{19}H_{30}O_2$ | 2.20 | 36.9 ± 1.47 | 35.7 ± 1.06 |
| ZINC04298453 | 309.33 | $C_{19}H_{16}FNO_2$ | 22.0 | 38.0 ± 2.01 | 39.4 ± 1.53 |

[a]determined by docking;
[b]determined by blocking assays; the data were indicated by mean ± standard deviation.

Figure 2:
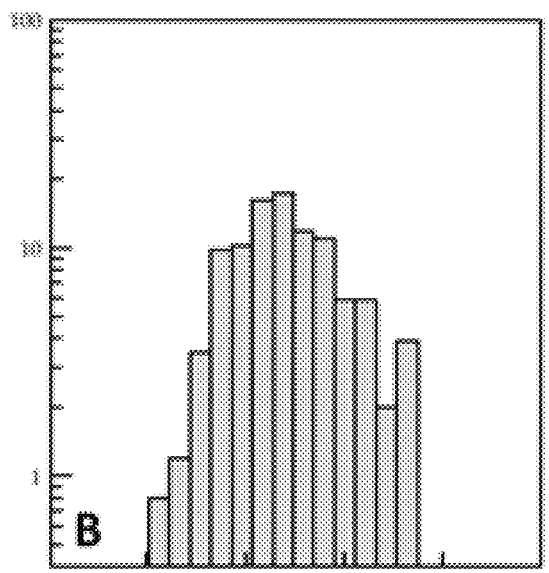
FIG. 2 is a graph showing the distribution of the lowest Ki values of the top 255 compounds docked at the HBGA binding sites of the VA387 P dimer.
Figure 3A:
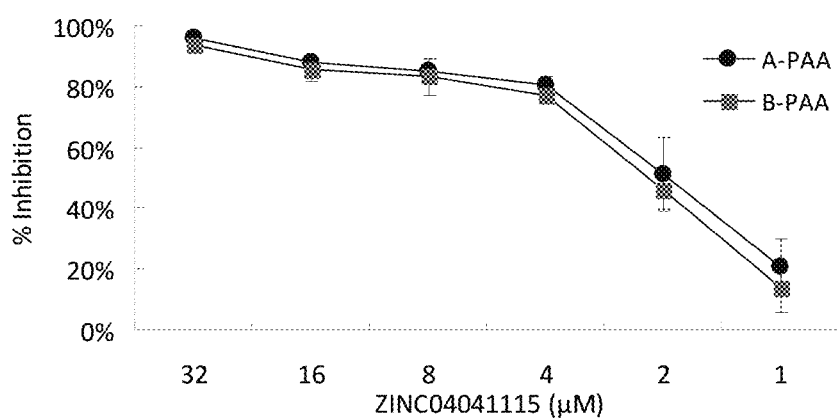
FIG. 3A depicts validation and titration of inhibitory activities of ZINC04041115 to HBGA oligosaccharide-PAA conjugates.
Figure 3B:
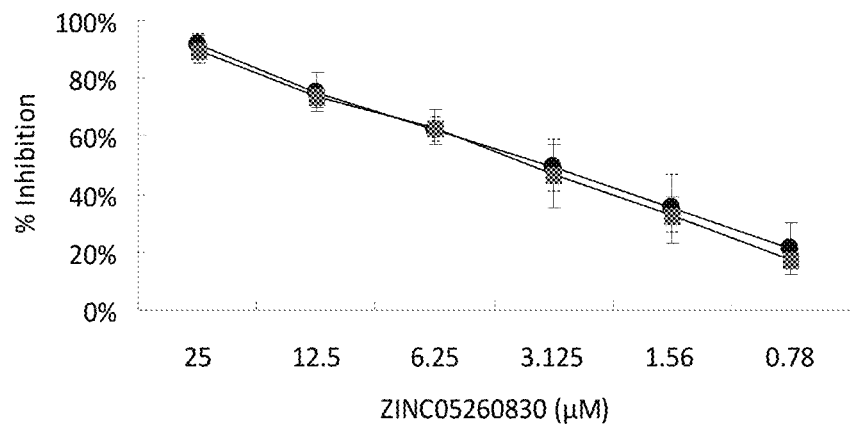
FIG. 3B depicts validation and titration of inhibitory activities of ZINC05260830 to HBGA oligosaccharide-PAA conjugates.
Figure 3C:
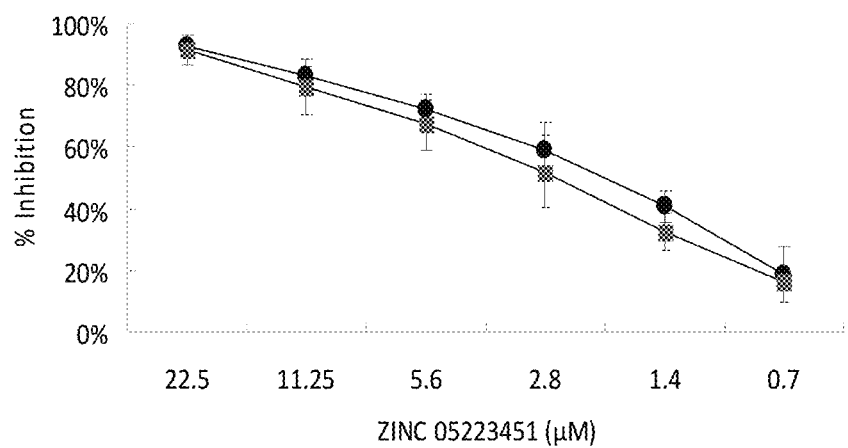
FIG. 3C depicts validation and titration of inhibitory activities of ZINC05223451 to HBGA oligosaccharide-PAA conjugates.
Figure 3D:
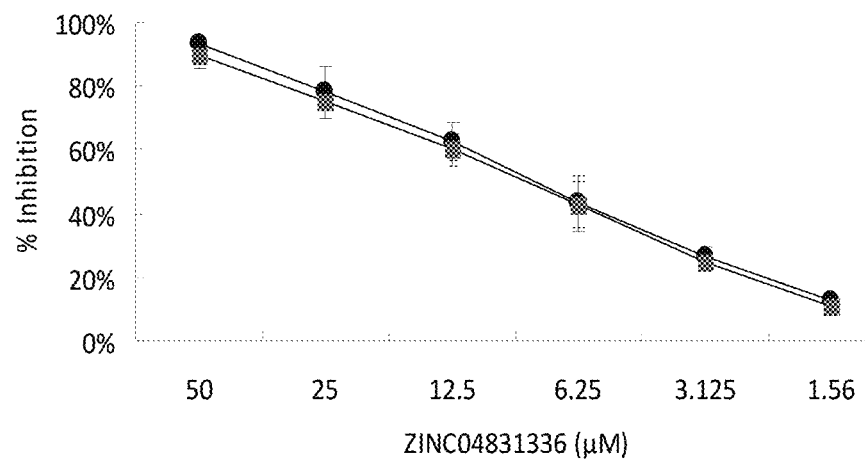
FIG. 3D depicts validation and titration of inhibitory activities of ZINC04831336 to HBGA oligosaccharide-PAA conjugates.
Figure 3E:
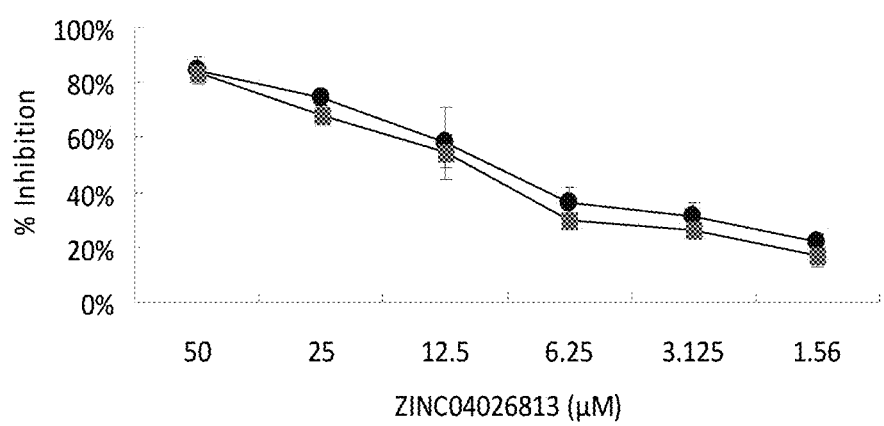
FIG. 3E depicts validation and titration of inhibitory activities of ZINC04026813 to HBGA oligosaccharide-PAA conjugates.

All of the top five strongest inhibitors (ZINC04041115, ZINC05260830, ZINC05223451, ZINC04831336 and ZINC04026813) revealed similar levels of inhibition in a dose-dependent manner against the VA387 P dimer binding to the synthetic A and B oligosaccharides. FIG. 2 shows validation and titration of inhibitory activities of the top 5 hit compounds to HBGA oligosaccharide-PAA conjugates. All compounds revealed significantly blocking activities against VA387 binding to the oligosaccharide-PAA conjugated A and B. The concentrations of the compounds used in the assays were adjusted according to their blocking activities in the type A and type B saliva screening. The IC50 concentrations of these 5 compounds were lower than 10 μM. Triplicate tests for each compound were performed, and the mean reduction of binding activity was presented. A marginal correlation between the $IC_{50}$ values from the block assays and the $K_i$ values from the docking simulation of the 20 top-list compounds were observed (Spearman r=0.561, p=0.01, data not shown).

Structure Comparisons of the Top 20 Hit Compounds.

The chemical structure of the 20 top-list compounds are shown in Table 1 according to their $IC_{50s}$ in blocking the binding of NoV P dimer to HBGAs. Interestingly, over a half of them share the basic structure of cyclopenta [a] dimethyl phenanthren, also depicted in Table 1. Particularly, four of the five most potent inhibitors share this common structure, suggesting that the cyclopenta [a] phenanthren with dimethyl may represent a promising class of compounds for further refinement.

The Cytotoxicity of Top 5 Hit Compounds.

This was tested in human cervical carcinoma cells (HeLa) and rhesus monkey kidney epithelial cells (LLC-MK2). The resulting $CC_{50s}$ were 203.2 (ZINC04041115), 266.8 (ZINC05260830), 170.6 (ZINC05223451), 225 (ZINC04831336) and 212.4 (ZINC04026813)μM, respectively.

We described in this study a search for inhibitors to NoV binding to HBGAs for antivirals against NoVs. The computer-aided drug development (CADD) approach was used. Computational models of NoV P dimers and their ligands (A and B trisaccharides) were constructed based on available crystal structures [6]. After validation of the models and docking protocol, over two million compounds in the ZINC library were screened by docking simulations and virtual screening. A total of 255 hit candidates have been identified, among which 160 were further tested by HBGA blocking assays. Twenty compounds (12.5%) exhibited >50% inhibitory effects (IC50) at concentrations below 40 μM, in which five have an IC50<10 μM. This study suggests the CADD is a useful approach for antiviral design against NoVs.

Virtual screening based on validated computer models allows elimination of undesired molecules from large compound libraries, thus greatly reducing the cost and time of drug discovery process. In our case, experimentally screening of a library with more than two million compounds is impossible due to the huge workloads. However, the VHTS approach resulted in only 255 hit candidates with theoretical binding affinity higher than the native HBGA ligands within a few weeks of computation time, which greatly facilitated our study to the next step of biological assays for validation. Nevertheless, computer-aided virtual screening also has shortcomings. For example, some active compounds or structures may be screened off by virtual screening and thus may not be tested. This limitation should be kept in mind when the CADD is used.

Five compounds were identified with high affinities (IC50s<10 μM) to the HBGA binding sites of GII.4 NoVs. Further development of affective antivirals against NoVs based on these top five compounds may be possible. All the five top candidates have the common structures of steroid pregnanolone which needs to be considered in our future studies for potential side effects of hormone activities of the candidates as well as their derivatives.

In our docking simulations using the A or B trisaccharide as ligands, both ligands were docked to an undefined nearby site around Arg 289. This type of extra docking site is understandable because the protein/carbohydrate interactions involve conformational network interactions and a single amino acid difference can significantly change the outcome of HBGA interaction in our mutagenesis studies of the HBGA binding interface of NoVs [4, 7, 8, 15, 16, 38, 39]. Because the receptor binding sites of human NoVs are highly conserved and the extra site was not found in any crystal structures of known NoVs. Thus, this extra docking site was ignored in our study.

The shared structures of cyclopenta [a] dimethyl phenanthren among most hit compounds suggest an important lead class of compounds for future development, although such structures also shared with the steroid pregnanolone. The low toxicity of all the top five compounds to HeLa and LLC-MK2 cells further suggest this basic structure may be a promising lead class.

Human NoVs are diverse in recognizing different HBGAs. However, the receptor binding interfaces of different NoVs are genetically and structurally conserved among strains within genogroups of major human NoVs. This suggests that the CADD approach described in this study may be extended to other NoVs recognizing different HBGAs because of potential common mechanism of virus/HBGA interaction for all human NoVs. In addition to the GII.4 NoVs that were explored in this study, the crystal structures of several other NoVs with different genetic backgrounds and HBGA binding profiles have also been determined, including the GI.1 Norwalk virus [5,8], GI.2 FUV258 [11], GII.9 VA207 [7], GII.10 Vietnam 026 [10] and GII.12 Hiro [10]. Future studies to develop antivirals for other NoVs using the same CADD procedures described in this study may be fruitful, because a good correlation between the IC50s in the blocking assays and the Ki values by the docking simulations has been found which support the VHTS as a useful approach for antiviral development against NoVs.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

REFERENCES

1. Glass R I, Parashar U D, Estes M K (2009) Norovirus gastroenteritis. N Engl J Med 361: 1776-1785.
2. Lopman B, Gastanaduy P, Park G W, Hall A J, Parashar U D, et al. (2012) Environmental transmission of norovirus gastroenteritis. Curr Opin Virol 2: 96-102.
3. Patel M M, Widdowson M A, Glass R I, Akazawa K, Vinje J, et al. (2008) Systematic literature review of role of noroviruses in sporadic gastroenteritis. Emerg Infect Dis 14: 1224-1231.
4. Tan M, Hegde R S, Jiang X (2004) The P domain of norovirus capsid protein forms dimer and binds to histo-blood group antigen receptors. J Virol 78: 6233-6242.
5. Bu W, Mamedova A, Tan M, Xia M, Jiang X, et al. (2008) Structural basis for the receptor binding specificity of Norwalk virus. J Virol 82: 5340-5347.
6. Cao S, Lou Z, Tan M, Chen Y, Liu Y, et al. (2007) Structural basis for the recognition of blood group trisaccharides by norovirus. J Virol 81: 5949-5957.
7. Chen Y, Tan M, Xia M, Hao N, Zhang X C, et al. (2011) Crystallography of a lewis-binding norovirus, elucidation of strain-specificity to the polymorphic human histo-blood group antigens. PLoS pathogens 7: e1002152.
8. Choi J M, Hutson A M, Estes M K, Prasad B V (2008) Atomic resolution structural characterization of recognition of histo-blood group antigens by Norwalk virus. Proc Natl Acad Sci USA 105: 9175-9180.
9. Shanker S, Choi J M, Sankaran B, Atmar R L, Estes M K, et al. (2011) Structural analysis of histo-blood group antigen binding specificity in a norovirus GII.4 epidemic variant: implications for epochal evolution. J Virol 85: 8635-8645.
10. Hansman G S, Biertumpfel C, Georgiev I, McLellan J S, Chen L, et al. (2011) Crystal Structures of GII.10 and GII.12 Norovirus Protruding Domains in Complex with Histo-Blood Group Antigens Reveal Details for a Potential Site of Vulnerability. J Virol 85: 6687-6701.
11. Kubota T, Kumagai A, Ito H, Furukawa S, Someya Y, et al. (2012) Structural basis for the recognition of Lewis antigens by genogroup I norovirus. J Virol 86: 11138-11150.
12. Tan M, Fang P, Chachiyo T, Xia M, Huang P, et al. (2008) Noroviral P particle: Structure, function and applications in virus-host interaction. Virology 382: 115-123.
13. Tan M, Fang P A, Xia M, Chachiyo T, Jiang W, et al. (2011) Terminal modifications of norovirus P domain resulted in a new type of subviral particles, the small P particles. Virology 410: 345-352.
14. Tan M, Jiang X (2005) The p domain of norovirus capsid protein forms a subviral particle that binds to histo-blood group antigen receptors. Journal of Virology 79: 14017-14030.
15. Tan M, Xia M, Cao S, Huang P, Farkas T, et al. (2008) Elucidation of strain-specific interaction of a GII-4 norovirus with HBGA receptors by site-directed mutagenesis study. Virology 379: 324-334.
16. Tan M, Xia M, Chen Y, Bu W, Hegde R S, et al. (2009) Conservation of carbohydrate binding interfaces: evidence of human HBGA selection in norovirus evolution. PLoS ONE 4: e5058.
17. Zheng D P, Widdowson M A, Glass R I, Vinje J (2010) Molecular epidemiology of genogroup II-genotype 4 noroviruses in the United States between 1994 and 2006. J Clin Microbiol 48: 168-177.
18. Tan M, Jiang X (2005) Norovirus and its histo-blood group antigen receptors: an answer to a historical puzzle. Trends Microbiol 13: 285-293.
19. Tan M, Jiang X (2007) Norovirus-host interaction: implications for disease control and prevention. Expert Rev Mol Med 9: 1-22.
20. Tan M, Jiang X (2010) Norovirus gastroenteritis, carbohydrate receptors, and animal models. PLoS pathogens 6: e1000983.
21. Tan M, Jiang X (2011) Norovirus-host interaction: Multi-selections by human histo-blood group antigens. Trends in microbiology 19: 382-388.
22. Tan M, Meller J, Jiang X (2006) C-terminal arginine cluster is essential for receptor binding of norovirus capsid protein. Journal of Virology 80: 7322-7331.
23. Irwin J J, Shoichet B K (2005) ZINC—a free database of commercially available compounds for virtual screening. J Chem Inf Model 45: 177-182.

24. Chen J H, Linstead E, Swamidass S J, Wang D, Baldi P (2007) ChemDB update—full-text search and virtual chemical space. Bioinformatics 23: 2348-2351.
25. Feng Z K, Chen L, Maddula H, Akcan O, Oughtred R, et al. (2004) Ligand Depot: a data warehouse for ligands bound to macromolecules. Bioinformatics 20: 2153-2155.
26. Biesiada J, Porollo A, Velayutham P, Kouril M, Meller J (2011) Survey of public domain software for docking simulations and virtual screening. Human genomics 5: 497-505.
27. Cavasotto C N, Orry A J W (2007) Ligand docking and structure-based virtual screening in drug discovery. Current topics in medicinal chemistry 7: 1006-1014.
28. Villoutreix B O, Eudes R, Miteva M A (2009) Structure-based virtual ligand screening: recent success stories. Combinatorial chemistry & high throughput screening 12: 1000-1016.
29. Wolf A, Shahid M, Kasam V, Ziegler W, Hofmann-Apitius M (2010) In silico drug discovery approaches on grid computing infrastructures. Current clinical pharmacology 5: 37-46.
30. Morris G M, Goodsell D S, Halliday R S, Huey R, Hart W E, et al. (1998) Automated docking using a Lamarckian genetic algorithm and an empirical binding free energy function. Journal of Computational Chemistry 19: 1639-1662.
31. Chang D T, Oyang Y J, Lin J H (2005) MEDock: a web server for efficient prediction of ligand binding sites based on a novel optimization algorithm. Nucleic Acids Res 33: W233-238.
32. Biesiada J, Porollo A, Meller J (2012) On setting up and assessing docking simulations for virtual screening. Methods in molecular biology (Clifton, N J) 928: 1-16.
33. Hetenyi C, van der Spoel D (2002) Efficient docking of peptides to proteins without prior knowledge of the binding site. Protein science: a publication of the Protein Society 11: 1729-1737.
34. Huang P, Farkas T, Zhong W, Tan M, Thornton S, et al. (2005) Norovirus and histo-blood group antigens: demonstration of a wide spectrum of strain specificities and classification of two major binding groups among multiple binding patterns. J Virol 79: 6714-6722.
35. Zhang X F, Dai Y C, Zhong W, Tan M, Lv Z P, et al. (2012) Tannic acid inhibited norovirus binding to HBGA receptors, a study of 50 Chinese medicinal herbs. Bioorg Med Chem 20: 1616-1623.
36. Taube S, Perry J W, McGreevy E, Yetming K, Perkins C, et al. (2012) Murine noroviruses bind glycolipid and glycoprotein attachment receptors in a strain-dependent manner. J Virol 86: 5584-5593.
37. Feng X, Jiang X (2007) Library screen for inhibitors targeting norovirus binding to histo-blood group antigen receptors. Antimicrob Agents Chemother 51: 324-331.
38. Tan M, Huang P, Meller J, Zhong W, Farkas T, et al. (2003) Mutations within the P2 domain of norovirus capsid affect binding to human histo-blood group antigens: evidence for a binding pocket. J Virol 77: 12562-12571.
39. de Rougemont A, Ruvoen-Clouet N, Simon B, Estienney M, Elie-Caille C, et al. (2011) Qualitative and quantitative analysis of the binding of GII.4 norovirus variants onto human blood group antigens. J Virol 85: 4057-4070.

What is claimed is:

1. A composition for use in inhibiting the binding of a Norovirus to the histo-blood group antigen on the surface of epithelia, the composition comprising at least about 5% by weight of a binding-inhibiting compound (ZINC0404115)

or a pharmaceutically acceptable salt thereof, and a pharmaceutically acceptable carrier and/or excipient.

2. The composition of claim 1, wherein said compound selectively binds to an oligosaccharide-PAA conjugated A and B compared to a VA-387P norovirus dimer.

* * * * *